United States Patent
Gladish et al.

(10) Patent No.: US 10,532,548 B2
(45) Date of Patent: Jan. 14, 2020

(54) FUNCTIONAL BIOMATERIAL COATINGS FOR TEXTILES AND OTHER SUBSTRATES

(71) Applicant: The North Face Apparel Corp., Wilmington, DE (US)

(72) Inventors: Justin Lee Gladish, Portland, OR (US); Mary-Ellen Smith, Kihei, HI (US)

(73) Assignee: The North Face Apparel Corp., Wilmington, DE (US)

( * ) Notice: Subject to any disclaimer, the term of this patent is extended or adjusted under 35 U.S.C. 154(b) by 477 days.

(21) Appl. No.: 15/029,903

(22) PCT Filed: Oct. 14, 2014

(86) PCT No.: PCT/US2014/060465
§ 371 (c)(1),
(2) Date: Apr. 15, 2016

(87) PCT Pub. No.: WO2015/061079
PCT Pub. Date: Apr. 30, 2015

(65) Prior Publication Data
US 2016/0250831 A1    Sep. 1, 2016

Related U.S. Application Data

(60) Provisional application No. 61/893,619, filed on Oct. 21, 2013.

(51) Int. Cl.
*B32B 27/36*    (2006.01)
*C07K 14/435*    (2006.01)
(Continued)

(52) U.S. Cl.
CPC .............. *B32B 27/36* (2013.01); *B32B 9/025* (2013.01); *C07K 14/43518* (2013.01);
(Continued)

(58) Field of Classification Search
CPC ... B32B 27/36; B32B 9/025; C07K 14/43518; C07K 14/47; D06M 10/025; D06M 10/10; D06M 15/15; D06M 16/00
(Continued)

(56) References Cited

U.S. PATENT DOCUMENTS 5,728,810 A    3/1998    Randolph et al.
5,733,771 A    3/1998    Lewis et al.
(Continued)

FOREIGN PATENT DOCUMENTS

CN    101018806    8/2007
JP    11-162440 A    6/1999
(Continued)

OTHER PUBLICATIONS

Hayashi et al. "Evidence from Flagelliform Silk cDNA for the Structural Basis of Elasticity and Modular Nature of Spider Skills". J. Mol. Biol. 275(5):773-84, Feb. 6, 1998.
(Continued)

*Primary Examiner* — Vincent Tatesure
(74) *Attorney, Agent, or Firm* — Ganz Pollard, LLC

(57) ABSTRACT

In some aspects, the inventive subject matter contemplates: providing a substrate; providing a biomaterial to be affixed to the substrate; and subjecting the substrate and biomaterial to reactive species from a plasma generated by an atmospheric plasma apparatus until the biomaterial affixes to the substrate. The biomaterial may be silk or wool polypeptide. The biomaterial is deposited as a monomeric film on the surface of the substrate before the substrate is subjected to the reactive species of the plasma. Once the substrate with the film of biomaterial is subjected to the reactive species, the reactive species facilitates the polymerization of the film as a coating on the underlying portion of substrate. The resulting coated substrates are novel constructs that have (Continued)

1. A series of Applicators/ plasma sources could be used or substrate could be reversed in a single setup of application/plasma source
2. Applicator and plasma source could be in same chamber or enclosure. Applicator and plasma source could be in simultaneous operation or sequential operation.

improved attributes based on the biomaterial selected for use. For example, silk proteins may be used improve the hand or strength of textile materials.

13 Claims, 5 Drawing Sheets

(51) Int. Cl.
| | | |
|---|---|---|
| *D06M 10/02* | (2006.01) | |
| *D06M 16/00* | (2006.01) | |
| *D06M 10/10* | (2006.01) | |
| *D06M 15/15* | (2006.01) | |
| *D02G 3/36* | (2006.01) | |
| *B32B 9/02* | (2006.01) | |

(52) U.S. Cl.
CPC ............ *D02G 3/36* (2013.01); *D06M 10/025* (2013.01); *D06M 10/10* (2013.01); *D06M 15/15* (2013.01); *D06M 16/00* (2013.01); *B32B 2255/26* (2013.01); *B32B 2262/08* (2013.01); *B32B 2307/202* (2013.01); *B32B 2375/00* (2013.01); *B32B 2437/00* (2013.01); *D06M 2200/11* (2013.01); *D06M 2200/12* (2013.01); *D06M 2200/25* (2013.01); *D06M 2200/50* (2013.01); *D06M 2400/01* (2013.01)

(58) Field of Classification Search
USPC .......................................................... 442/102
See application file for complete search history.

(56) References Cited

U.S. PATENT DOCUMENTS

| | | | |
|---|---|---|---|
| 5,756,677 | A | 5/1998 | Lewis et al. |
| 5,989,894 | A | 11/1999 | Lewis et al. |
| 5,994,099 | A | 11/1999 | Lewis et al. |
| 7,057,023 | B2 | 6/2006 | Islam et al. |
| 7,868,146 | B2 | 1/2011 | Scheibel et al. |
| 8,016,894 | B2 | 9/2011 | Selwyn et al. |
| 8,361,275 | B2 | 1/2013 | Tahara et al. |
| 8,361,276 | B2 | 1/2013 | Selwyn |
| 2004/0152381 | A1 | 8/2004 | York et al. |
| 2008/0107822 | A1 | 5/2008 | Selwyn et al. |
| 2009/0286435 | A1 | 11/2009 | Badyal et al. |
| 2010/0151114 | A1 | 6/2010 | Parrott |
| 2012/0190260 | A1* | 7/2012 | Morishita ............. D03D 15/08 442/301 |
| 2012/0252294 | A1 | 10/2012 | Leimer et al. |
| 2013/0068690 | A1 | 3/2013 | McCord et al. |

FOREIGN PATENT DOCUMENTS

| | | | |
|---|---|---|---|
| JP | 2000031766 | A | 1/2000 |
| JP | 2001214370 | A | 8/2001 |
| JP | 2002201297 | A | 7/2002 |
| JP | 2004143649 | | 5/2004 |
| JP | 2008518105 | A | 5/2008 |
| WO | WO2006002827 | | 1/2006 |
| WO | WO2006008163 | | 1/2006 |
| WO | WO2006117829 | | 11/2006 |
| WO | WO2007025719 | | 3/2007 |
| WO | WO2007031301 | | 3/2007 |

OTHER PUBLICATIONS

Hinman et al. "Synthetic Spider Silk: A Modular Fiber". Trends in Biotech. 18(9): 374-379, Sep. 2000.
Vollrath et al. "Compounds in the Droplets of the Orb Spider's Viscid Spiral". Nature 345: 526-528, 1990.
Vollrath. "Strength and Structure of Spiders' Silks". Reviews in Molecular Biology. 74(2):67-83, 2000.
Trade show: http//www.aatcc.org/events/symposia/IFAISeminar. htm.
Salas et al. "Water-Wettable Polypropylene Fibers by Facile Surface Treatment Based on Soy Protein". ACS Applied Materials & Interfaces 5(14): 6541-6548, Jul. 24, 2013.
Goli et al. "Generation of Functional Coatings on Hydrophobic Surfaces through Deposition of Denatured Proteins Followed by Grafting from Polymerization". Biomacromolecules 2012, 13, 1371-1382.
Chinta et al. "Plasma technology & its application in textile web processing". International Journal of Engineering Research Technology (IJERT). vol. 1, Issue 5. Jul. 2012.
Saravanan. "Spider silk—structure, properties and spinning". Journal of Textile and Apparel, Technology and Management. vol. 5, Issue 1, Winter 2006.
International Search Report and Written Opinion of the International Searching Authority in International Application No. PCT/US14/060465 dated Feb. 6, 2015.
International Preliminary Report on Patentability in International Application No. PCT/US14/060465 dated Apr. 26, 2016.
Second Office Action with English Translation in Chinese Application No. 2014800698628, dated Jan. 5, 2018, 11 pages.
Extended European Search Report for European Application No. 14855947.9, dated Aug. 21, 2017, 11 pages.
Young Woo Cheon et al., "Enhanced Chondrogenic Responses of Human Articular Chondrocytes Onto Silk Fibroin/Wool Keratose Scaffolds Treated With Microwave-Induced Argon Plasma," Artificial Organs, May 5, 2010, pp. 384-392, vol. 34, No. 5, Wiley Online Libray.
Demura M et al, "Characterization of Low-Temperature Plasma Treated Silk Fibroin Fabrics by ESCA and the Use of the Fabrics as an Enzyme-Immobilization Support," Biomaterials, Jan. 1, 1992, pp. 276-277, vol. 13, No. 5, Elsevier Science Publishers BV, Barking, GB.
Office Action or European Application No. 14855947.9, dated Apr. 12, 2018, 6 pages.
Japanese Office Action dated Feb. 14, 2017 in Japanese Application No.
Chinese Office Action dated Mar. 17, 2017 in Chinese Application No.

* cited by examiner

FUNCTIONAL BIOMATERIAL COATINGS FOR TEXTILES AND OTHER SUBSTRATES

RELATED APPLICATIONS

This application claims the benefit of and priority to U.S. Provisional Application Ser. No. 61/893,619, filed Oct. 21, 2013 the contents of which are hereby incorporated by reference as if recited in full herein for all purposes.

BACKGROUND

The inventive subject matter relates to functional biomaterial coatings for textiles and other substrates. It particularly relates to the application of silk polypeptides, especially natural or synthetic spider silk polypeptides to textile surfaces. The inventive subject matter may use plasmas generated in atmospheric pressure systems to facilitate the formation of the coatings.

Modern textiles are designed to impart selected properties to end products. For example, for apparel products selected properties may include: waterproofness, breathability, windproofness, thermal retention, elasticity, durability, dyeability, comfort, UV resistance, etc. In the case of modern outdoor gear, there is a demand for multiple such properties in a given garment. However, providing one given property may be at the cost of providing another. For example, waterproof garments use materials that tend to be stiff and not comfortable against a user's skin. The most breathable garments tend not be waterproof. Softer, more comfortable garments tend not to be the most durable. Achieving multiple objectives is therefore exceedingly difficult in a single layer of textile material. Therefore, garments that do so typically are made in multiple layers or with multiple coatings of material deposited on a given textile layer. The use of such multiple layers creates extra and inefficient manufacturing steps and cost, extra weight and bulk, among other disadvantages.

In respect of the foregoing, there is a particular need to improve the haptic experience users have with known or to be discovered textile materials. In the apparel industry, the sensory experience has been referred to as the "hand" of fabrics. Hand may generally be defined as "the quality of a fabric assessed by the reaction obtained from the sense of touch." Other areas having a need for efficient and simplified construction of end products with multiple properties include bed linens, table linens, upholstery, drapery, tents, awnings, etc.

Accordingly, there is a substantial need for improved textile constructions and manufacturing methods that address the aforementioned needs. These and various other needs are addressed by the inventive subject matter disclosed herein.

SUMMARY

In general, the inventive subject matter relates to methods of treating a substrate, such as a textile to improve substrate properties. In some aspects, the inventive subject matter contemplates providing a substrate having a generally sheet or planar form; providing a biomaterial to be affixed to the substrate, and subjecting the substrate and biomaterial to reactive species from a plasma generated by an atmospheric plasma apparatus until the biomaterial affixes to the substrate. The substrate may include biomaterial, such as silk polypeptide. The biomaterial is deposited as a monomeric film on the surface of the substrate before the substrate is subjected to the reactive species of the plasma. Once the substrate with the film of biomaterial is subjected to the reactive species, the reactive species facilitates the polymerization of the film as an coating on the underlying portion of substrate. The resulting coated substrates are novel constructs that have improved attributes based on the biomaterial selected for use. For example, silk proteins may be used improve the hand or strength of textile materials.

In some of its possible embodiments, the inventive subject matter is generally directed to the coating of textile materials with polypeptides that impart new properties to the textile while not necessarily negating the textile's existing properties or characteristics. Coatings based on polypeptides or proteins of various natural or synthetics silks (e.g., moth or spider silk) are specifically contemplated under the inventive subject matter. The textiles are not limited to any particular type. As used herein, "textile" is used in the broadest sense, namely a woven, knit, felted or other woven or non-woven thin sheet of pliable material useful like a fabric or cloth in finished articles such as items of apparel, footwear, and upholstery and components thereof. The textiles may consist of synthetic fibers, natural fibers, blends, as well as bio-based fiber materials. The textiles may be used in any number of applications, including for casual, business or uniform apparel, home furnishings, furniture or transportation upholstery, hospitality items, such as table linens or napkins, carpets, felts, outdoor furniture, tarps or sunscreens, and any other fibrous items. Fabrics may be flexible, fibrous non-woven substrates, such as paper and paper bandages, disposable apparel or wipes.

In some of its possible embodiments, the inventive subject matter relates to surface modification of woven and non-woven textiles as substrates (which may also be referred to herein as "workpieces") in a plasma processing operation. The class of plasma processing operations known as "atmospheric plasma" processing is particularly suitable for creating such modifications. Modifications in the nature of applying polypeptide or protein coatings to substrate surfaces are particularly contemplated by the inventive subject matter.

In some embodiments, plasma processing is used to deposit and cure new functional proteins onto the fabric surface. For example, by depositing silk polypeptide or proteins onto a fabric, the hand of the fabric may be altered and/or the strength of the fabric increased. Accordingly, in some embodiments, the inventive subject matter is directed to improving the hand of textiles with respect to predetermined hand or haptic attributes, e.g., smoothness, friction, elasticity, thermal conductivity, and any other tactile attribute. Changing hand feel by plasma deposition includes the deposition of not only synthetic and natural proteins, but also cellulosic materials, and biomaterials yet to be developed.

These and other embodiments are described in the following detailed descriptions and the figures.

The foregoing is not intended to be an exhaustive list of embodiments and features of the inventive subject matter. Persons skilled in the art are capable of appreciating other embodiments and features from the following detailed description in conjunction with the drawings.

The following is a description of various inventive lines under the inventive subject matter. The appended claims, as originally filed in this document, or as subsequently amended, are hereby incorporated into this Summary section as if written directly in.

BRIEF DESCRIPTION OF THE DRAWINGS

The following figures show embodiments according to the inventive subject matter, unless noted as showing prior art.

DETAILED DESCRIPTION

Overview

Figure 1:
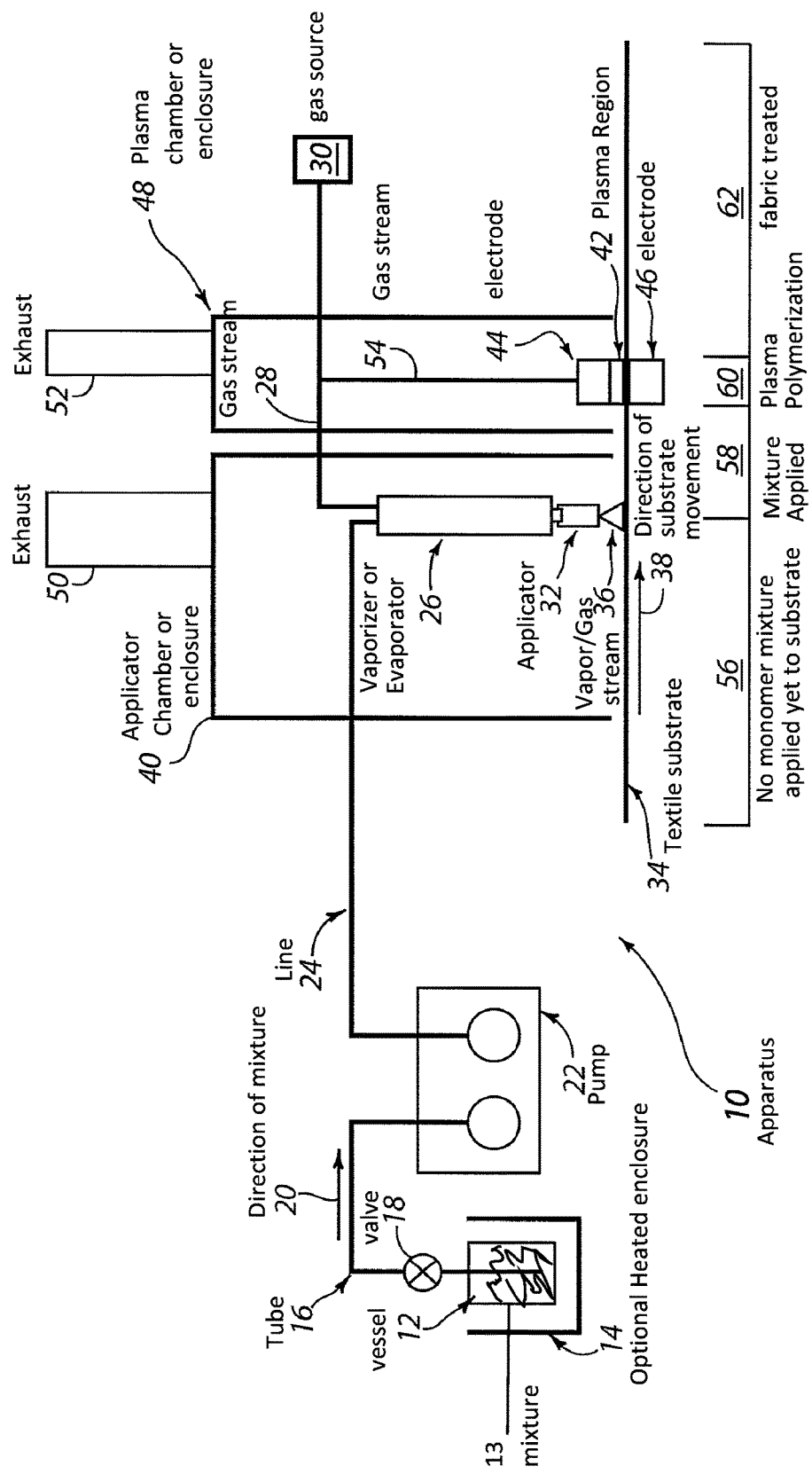
FIG. 1 is a schematic representation of a prior art apparatus that may be adapted for use in a method according to the inventive subject matter of treating substrates with a biomaterial under a plasma operation.

Persons skilled in the art will recognize that many modifications and variations are possible in the details, materials, and arrangements of the parts and actions which have been described and illustrated in order to explain the nature of the inventive subject matter, and that such modifications and variations do not depart from the spirit and scope of the teachings and claims contained therein.

In some of its possible embodiments, the inventive subject matter is generally directed to the coating of substrate materials with polypeptides that impart new properties to the textile while not necessarily negating the textile's existing properties. Coatings based on biomaterials are contemplated under the inventive subject matter. Coatings based on polypeptides or proteins of various natural or synthetics silks (e.g., moth or spider silk) are specifically contemplated under the inventive subject matter. The substrates specifically contemplated under the inventive subject matter include textile. The textiles are not limited to any particular type. As used herein, "textile" is used in the broadest sense, namely a woven, knit, felted or other woven or non-woven thin sheet of pliable material useful like a fabric or cloth in finished articles such as items of apparel, footwear, and upholstery. The textiles may consist of synthetic fibers, natural fibers, blends, as well as bio-based fiber materials.

In some of its possible embodiments, the inventive subject matter relates to surface modification of woven and non-woven textiles as substrates (which may also be referred to herein as "workpieces") in a plasma processing operation. The class of plasma processing operations known as "atmospheric plasma" processing is particularly suitable for creating such modifications. Modifications of textiles in the nature of applying polypeptide or protein coatings to textile surfaces are particularly contemplated by the inventive subject matter.

In various embodiments, plasma processing is used to deposit and cure functional proteins onto the fabric surface or other substrate surface. Creating a construct of biomaterial deposited on a textile substrate via plasma treatment is a novel approach to alter the haptic feedback or hand of fabrics, according to the inventive subject matter. Changing hand feel by plasma deposition includes the deposition of biomaterials that have desired physical properties. The biomaterials may include synthetic and natural proteins, cellulosic materials, as well as materials yet to be developed. For example, silk is known for smoothness and comfort. By depositing silk polypeptide or proteins onto a fabric, the hand of the fabric may be altered to impart the feel of silk. Accordingly, in some embodiments, the inventive subject matter is directed to improving the hand of textiles with respect to predetermined hand or haptic attributes, e.g., smoothness, friction, elasticity, thermal conductivity, and any other tactile attribute.

In some embodiments, plasma processing is used to deposit a substance on one or more surfaces of a textile to impart new functionalities to the resulting construct, which functionalities are in addition to or instead of modification of the hand of the fabric. For example, by depositing silk polypeptide or proteins onto a fabric, the strength or elasticity of the fabric may be altered. Accordingly, in some embodiments, the inventive subject matter is directed to improving the hand of textiles with respect to predetermined attributes, e.g., strength, elasticity, thermal retention, and other physical attributes.

Current textile wet processes are energy and resource intensive. Textile processes such as dyeing, applying water or stain repellency, and other surface treatments require large amounts of water and large amounts of energy for drying, and maintaining cure temperatures. The wet-dyeing equipment also has large footprint on the factory floor. Accordingly, there is a need for improved textile processes that use little or no water. There is a need also a need for such processes to require less energy and space, and fewer chemicals and byproducts. By selecting biomaterials of varying hydrophobicity/hydrophilicity plasma processing may be used to impart characteristics such as water repellency and dyeability. For example, polypeptides with natural or synthetic amino acids that are predominantly hydrophobic may impart water and/or stain repellency.

Plasma technology has been around since at least the 1960s. Plasma is generally considered a gaseous phase of matter characterized by excited species such ions, free electrons, and an amount of visible, UV and IR radiant energy. The plasma state can be generated by electrical energy, nuclear energy, thermal energy, mechanical energy and/or radiant energy. Plasmas may be characterized by charged particle density, temperature, pressure and the presence/absence of electrical and/or magnetic fields. Plasma is generally classified as thermal or non-thermal. In thermal plasma, temperature of several thousand degrees is reached, which is destructive of textiles and other common materials. Non-thermal plasmas may be referred to as "cold" plasmas because they may be maintained at low temperatures such as between 0-100 degrees Celsius range. There are two types of cold plasma that can be used in textile applications: low pressure, i.e., sub-atmospheric (approximately 1-100 pa), and atmospheric (ambient) pressure.

Atmospheric plasma is available in a number of different forms: corona treatment, dielectric barrier discharge, hybrid combinations, and atmospheric glow discharge. One disadvantage of low-pressure plasma treatments is that they are performed in a contained vessel, under vacuum. Therefore, they are limited to batch processing of textiles, not continuous processing. For the speed of processing textiles in a roll-to-roll process for large volumes, batch processing is not efficient. On the other hand, with recent advances in atmospheric plasma treatments, the possibility now exists for continuous processing of textiles. Because atmospheric plasma can be a roll-to-roll process and can mimic high temperature reactions at room temperature, it promises to be an ideal process to use for the modification of textiles.

Textiles often have limitations to high cure and process temperatures. Although many parameters influence the plasma treatment (plasma gas type, residence time, gas flow, frequency, power, pressure, ambient temperature, liquid monomers, gases), the process is a more energy efficient and environmentally friendly. The downside of conventional, high-temperature plasma processes is that the surface modification and molecular modification are limited by the aggressive nature of the plasma. The plasma destroys the molecular chains of the molecule injected into the plasma and fragments the material. Atmospheric plasma provides sufficient energy to create a coating that maintains the spaces between the yarns, withstands multiple home launderings, maintains the integrity of the fabric, and does not affect the air permeability of the fabric. The spaces between fibers in a woven fabric are on the order of 100 nm, and a film thickness of 70 nm would have negligible effect on the fabric breathability.

The ionized species in plasma can occur when a voltage is placed across the gas. Radicals present in the plasma react with the surface of a substrate and/or with other species in the plasma. Plasma reactions can transform substrate surfaces in various ways. The species and energy in the plasma may be used to etch or clean a substrate surface. The plasma may enable may cause various forms of substrate surface activation. For example, the plasma conditions may cause breaking of chemical bonds; grafting of chemical moieties and functional groups, volatilizing of surface materials and removal (etching), dissociating of surface contaminants/layers (cleaning/scouring), and depositing of conformal coatings. In all these processes a highly surface specific region of the textile material (e.g., <1000 A) is given new, desirable properties without negatively affecting the bulk properties of the constituent fibers or other constituent material. To illustrate a few textile applications, surfaces may be roughened or smoothed. They may be made more hydrophobic or more hydrophilic. Chemical modification of the surface can occur by the attachment of functional groups to the substrate surface. Plasma polymerization of thin films is also an option. During the plasma process, monomers or polymers can be linked together or polymerize at the substrate surface and provide thin films of various surface and technical performance alterations. Pre-treatment and surface modification can be accomplished using the plasma gas/substrate interaction. To apply thin films and functional groups, for instance, small amounts of the chemicals are injected via a syringe, or mist, into the plasma cloud. Certain gas plasmas are used for certain effects: Argon—surface roughness modifications; Oxygen—surface and surface energy modifications; Ammonia and carbon dioxide—surface chemical reactivity modifications. Using an inert gas plasma of helium is particularly suitable for monomers that polymerize via free radical reactions. An inert gas is able to trigger polymerization without chemically altering the polymer coating created. Additions of the aforementioned reactive gases ($H_2$, $N_2$, $NH_3$) can alter the performance and composition of the resulting polymer. These blends can induce condensation reactions or cross-linking of polymer chains. For example, the addition of $H_2$ could result in the condensation of a monomer via the loss of an OH group by way of a condensation reaction. Additionally, to increase the durability of the monomers, additions of $N_2$ and $NH_3$ may induce crosslinking of polymer chains. Proposed pathways of plasma-induced polymerization reactions induced between monomer-fabric or monomer-monomer polymerization have been documented in literature.

In addition to the application of biomaterials contemplated herein, plasma treatment has been used for the application of fabric treatments such as water repellent, flame retardant, and other finishes. The flame retardant and water repellent monomers may be mixed in a bath and applied to the substrate or they may be vaporized and applied in a plasma chamber. The finishes are then cured simultaneously using a plasma operation, such as atmospheric glow discharge plasma. Accordingly, additives may be concurrently or sequentially applied to substrates by the same plasma processes used to apply the biomaterials disclosed herein. The additives include primary, secondary, or higher order applications of one or more finishes of water repellents, antimicrobials, flame retardants, dye chemistry, and other fabric treatments. Therefore, the addition of one or more secondary functional finishes may be included in the protein monomer feedstocks contemplated herein or in a separately applied feedstock. For example, secondary finishes in a different feedstock may be added via additional passes through the atmospheric plasma.

The following is one possible embodiment for the introduction and curing of the protein monomers, and subsequently secondary finishes. In a first step pre-deposition step, a substrate, for example, a fabric, is subjected to a plasma pre-treatment that activates the fabric surface. In a second step, polypeptide monomers are deposited in the activated surface of the fabric in vapor form (or via a padding addition). In a third step, the fabric surface with the deposited monomer is subjected to a second plasma exposure to polymerize the monomer. This multi-step process may be used to optimize the monomer feed stock solution composition and plasma parameters, such as flow rate, etc., to the one-step process of passing the fabric through the plasma-monomer mix and allowing the deposition, polymerization or curing of the monomers on the fabric in a one-step plasma treatment step. Additionally, secondary finishes can be added to the fabric and feedstock solution under these processes.

Plasma conditions are at about room temperature and at about atmospheric pressure. The proteins and other biomaterials contemplated hereunder may be injected into a plasma chamber as a liquid spray or vapor or atomized particles and are expected to hold up to the plasma process conditions. When plasma is created, through a voltage addition, it creates active species, which collide with the textile surface. For the textile, plasma usually reacts with the carbon or heteroatoms of the substrate and can form active free radical functional groups. When the material (e.g., silk polypeptides) is injected into the plasma, it should bind and cure onto the active surface groups of the substrate via chemical bonding. For example, the material may be monomeric material that polymerizes on the surface of the substrate by forming bonds between monomers and/or with the substrate.

For fabric and like fiber-based substrates, because atmospheric plasma is at about room conditions, it is not necessary to pre-condition the fabric to humidity of the air. In some possible embodiments, the general process involves moving the fabric into the plasma chamber and subjecting the fabric to monomers at atmospheric pressure, followed by rapid polymerization, or curing, of the monomer on the fabric surface by the plasma to achieve a uniform coating that does not affect the drape or breathability of the fabric. The amount of monomer deposited (and/or polymerized) may depend on the flow rate of the monomer and the staged speed or residence time in the chamber under plasma conditions. Changes in the time spent in the chamber under plasma conditions can increase the thickness of the application. Furthermore, the process can be repeated numerous times to increase the thickness of the coating to impart the desired tactile feel without affecting the drape or stiffness of the fabric.

Generally, plasma may create short-lived activated species on the substrate surface. Because atmospheric plasma operations use free-radical chemistry at room temperature, polypeptides are expected to remain stable in plasma operations. However, it is possible that the proteins themselves could become activated in the plasma in a similar fashion to what has been seen with pre-treatment of wool fabric (also a protein). If both a protein and a fabric substrate are activated by plasma, the free radicals from each material could bind with each other and improve adhesion. If the activation of the proteins become problematic or destroy the protein material, it would be possible to alter the feed gas to specify the radical formation. Another possibility is to deposit the proteins onto the substrate as a monomer coating and use active species from the plasma as agents that polymerize the monomers together.

In short, the electric field of the plasma or active species generated by the electric field of the plasma apparatus could generate specific active groups and form active groups selectively on the protein dispersed in the plasma or on the substrate in communication with the plasma or active species of the plasma. The plasma may be used to polymerize monomers and to introduce onto the surface of substrates active species, such as hydroxyls, amines, peroxides, etc.

While atmospheric pressure plasmas typically use helium (e.g., for polymer deposition) as the carrier gas, others gases or blends can be used. However, helium is a small atom that can lack vibrational, electronic, and rotational energy levels sufficient to cause high ionization. Other gases may be used as a carrier gas in creating relatively high-energy plasmas. Such gases include ambient air, nitrogen, oxygen, argon, and any combination of these gases. These other carrier gases require relatively higher voltages, and might damage to textile substrates, so gases and process conditions will be selected accordingly.

Protein Depositions and Coatings

In some embodiments, the inventive subject matter is directed to methods of depositing biomaterials in the nature of monomers of polypeptides onto the surface of a textile material or other substrate, and polymerizing the monomers into a layer affixed to the surface of the substrate. Polypeptides that are characteristic of silk or wool are among those contemplated.

Unless otherwise indicated, the terms "polypeptide" and "protein" are used interchangeably herein and mean any peptide-linked chain of amino acids, regardless of length or post-translational modification.

The biotechnology for silk proteins is well established and includes much literature for creating synthetic silk from sources such as spider DNA. Accordingly, the following is a general discussion, along with a few detailed representative examples, based primarily on spider silks.

Spider silk is thought to have chemical reactivity similar to wool. Wool has been found to be usable, generally stable and able to form bonds under atmospheric plasma processing operations. Both wool and silk are proteins and share amino acids, which can be made into reactive groups under an electrical field.

Figure 4:
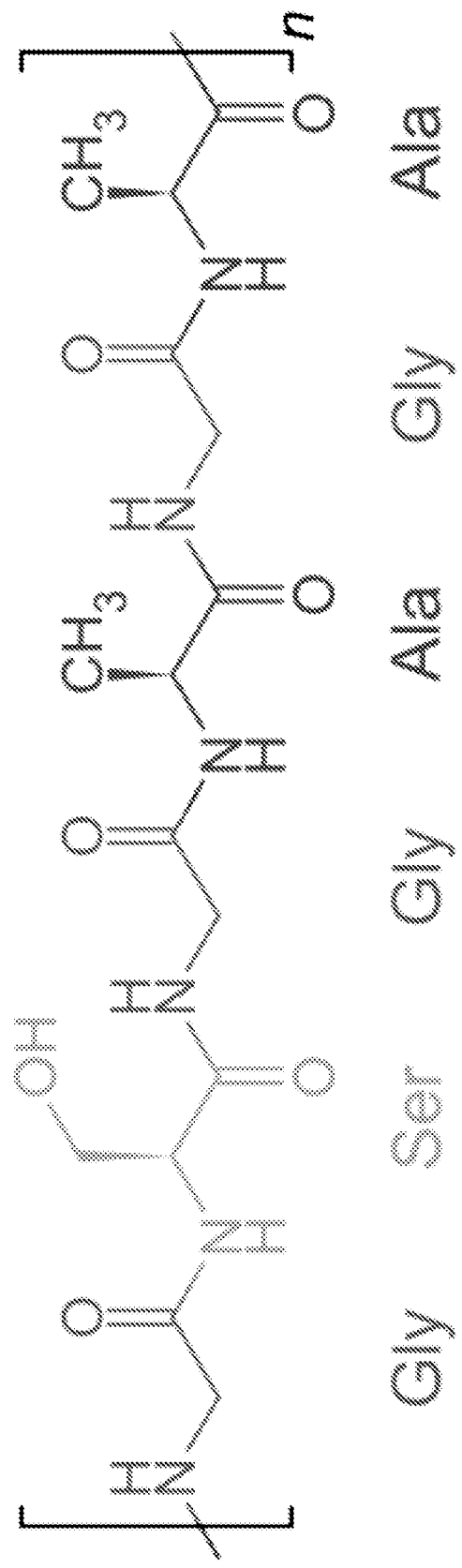
FIG. 4 shows a basic unit of fibroin protein.

One common silk is spider silk. One form of spider silk in its raw state consists of two main proteins, sericin and fibroin. Fibroin is the structural center of the silk, and sericin is the sticky material surrounding it. FIG. 4 shows the primary structure of fibroin, which is (Gly-Ser-Gly-Ala-Gly-Ala)$_n$. Fibroin is an insoluble protein created by not only spiders but also the moth larvae of *Bombyx mori*, other moth genera, such as *Antheraea, Cricula, Samia* and *Gonometa*, as well as numerous other insects. The fibroin protein consists of layers of antiparallel beta sheets. The high glycine (and, to a lesser extent, alanine) content allows for tight packing of the sheets, which contributes to silk's rigid structure and tensile strength. Fibroin is known to arrange itself in three structures, called silk I, II, and III. Silk I is the natural form of fibroin, as emitted from the *Bombyx mori* silk glands. Silk II refers to the arrangement of fibroin molecules in spun silk, which has greater strength and is often used in various commercial applications. Silk III is a newly discovered structure of fibroin. Silk III is formed principally in solutions of fibroin at an interface (i.e., air-water interface, water-oil interface, etc.).

Natural spider silk is produced out of a milk of polypeptide monomers. Polymerization occurs under a dehydrogenation process. The final step in the process is an elongation of the molecules. This elongation is under stress causing the molecules to join together by hydrogen bonds and to crystallize. During this process hydrophilic groups move to the interior, forcing out the excess water and hydrophobic groups in the process.

Solutions of synthetic silk protein bind similarly. During synthetic formation, hydrophobic effects (protein-protein interactions) of non-polar amino acids, dispersion forces, and electrostatic attractions from arginine residues contribute to the binding of fibroin molecules. Because of these molecular interactions described, and the ability to use plasma to alter the surface energy (hydrophobicity/hydrophilicity) of fibers and substrates, it is believed that the amino acid sequence in dragline spider silk will react similarly and perhaps have better reaction potential than wool fibers. Because spider silk is resistant to most common solvents and enzymes, using a plasma processing operation to apply silk to a fabric or other substrate is novel approach to material deposition and coating.

Because silk fibers gain structure on the loss of water, this disclosure also contemplates the application of silk proteins to a fabric surface via a water application using a controlled heat and cure step to remove the water and polymerize the silk onto the fiber surface.

In some embodiments, the silk proteins may be directly applied to a fabric, such as in a pad process, and a plasma operation may be used to cure directly the proteins on the fabric.

This disclosure includes the use of all bio-derived spider silks, silkworm silks, other arthropod silks, and mussel silks. It includes the use of a wide range of different amino acid combinations and blends or other synthetic, e.g. recombinant silk sources, as persons skilled in the will recognize are representative of silk proteins. The sources of protein include, but are not limited to, natural harvested biological sources and transgenic hosts, such as *E. coli*, mammalian cells (e.g., goat cells), and plant source, e.g. leaves, tubers, endoplasmic reticulum, etc.

The Table below shows comparative amino acid compositions of spider silk dragline and wool. These similarities, along with a myriad of research, display the consistency and feasibility for the reactivity and use of protein fibers (wool and silk) and plasma technology. While all types of silk share four types of amino acid motifs, spiders can synthesize up to seven types of silk. These types vary in elasticity, crystallinity, elasticity, with high and low strength. Therefore, as synthetic silks become commercially available, it is possible to tailor the silk for different properties. Due to the nature of this invention, all silks and combinations of their amino acid composition for different hand feel, elasticity, and strength are included in this disclosure. This includes compositions and blends of the following spider silks: Draglines, Visscid, Glue-like, minor, Cocoon, Wrapping, and Attachment silks.

TABLE 1

Amino Acid Composition (mole %) of Spider dragline silk and Other Protein Fibers

| Amino Acid | Sericin | Fibroin | Wool Keratin | Spider Silk |
|---|---|---|---|---|
| Glycine | 13.9 | 43.7 | 8.4 | 37.1 |
| Alanine | 5.9 | 28.8 | 5.5 | 21.1 |
| Valine | 2.7 | 2.2 | 5.6 | 1.8 |
| Leucine | 1.1 | 0.5 | 7.8 | 3.8 |
| Isoleucine | 0.7 | 0.7 | 3.3 | 0.9 |
| Serine | 33.4 | 11.9 | 11.6 | 4.5 |
| Theronine | 9.7 | 0.9 | 6.9 | 1.7 |
| Aspartic Acid | 16.7 | 1.3 | 5.9 | 2.5 |
| Glutamic Acid | 4.4 | 1.0 | 11.3 | 9.2 |
| Phenylanine | 0.5 | 0.6 | 2.8 | 0.7 |
| Tyrosine | 2.6 | 5.1 | 3.5 | — |
| Lysine | 3.3 | 0.3 | 2.6 | 0.5 |
| Histidine | 1.3 | 0.2 | 0.9 | 0.5 |
| Arginine | 3.1 | 0.5 | 6.4 | 7.6 |
| Proline | 0.6 | 0.5 | 6.8 | 4.3 |
| Tryptophan | 0.2 | 0.3 | 0.5 | 2.9 |
| Cystine | 0.1 | 0.2 | 9.8 | 0.3 |
| Methionine | 0.04 | 0.1 | 0.4 | 0.4 |

Sourced from: Amman, Bannari, *Spider Silk-Structure, Properties, and Spinning*, JTATM, Volume 5, Issue 1, Winter 2006.

As an illustrative example, U.S. Pat. No. 7,057,023 discloses various forms of spider silk polypeptides and methods and apparatus for spinning silk. Like other silks, spider silks are proteinaceous fibers composed largely of non-essential amino acids. Orb-web spinning spiders have as many as seven sets of highly specialized glands and produce up to seven different types of silk. Each silk protein has a different amino acid composition, mechanical property, and function. The physical properties of a silk fiber are influenced by the amino acid sequence, spinning mechanism, and environmental conditions in which it was produced.

Spider silk proteins are designated according to the gland or organ of the spider in which they are produced. Spider silks known to exist include major ampullate (MaSp), minor ampullate (MiSp), flagelliform (Flag), tubuliform, aggregate, aciniform, and pyriform spider silk proteins. Spider silk proteins derived from each organ are generally distinguishable from those derived from other synthetic organs by virtue of their physical and chemical properties. For example, major ampullate silk, or dragline silk, is extremely tough. Minor ampullate silk, used in web construction, has high tensile strength. An orb-web's capture spiral, in part composed of flagelliform silk, is elastic and can triple in length before breaking. Tubuliform silk is used in the outer layers of egg-sacs, whereas aciniform silk is involved in wrapping prey and pyriform silk is laid down as the attachment disk.

The biofilament proteins that may be used in the inventive subject matter include spider silk protein, including recombinantly produced major ampullate, minor ampullate, flagelliform, tubuliform, aggregate, aciniform and pyriform proteins. These proteins may be any type of biofilament proteins such as those produced by a variety of arachnids, including, but not limited to *Nephilla clavipes*, *Arhaneus* ssp. and *A. diadematus*. Also, as noted above, suitable for use in the invention are proteins produced by insects such as *Bombyx mori*. Dragline silk produced by the major ampullate gland of *Nephilia clavipes* occurs naturally as a mixture of at least two proteins, designated as MaSpI and MaSpII. Similarly, dragline silk produced by *A. diadematus* is also composed of a mixture of two proteins, designated ADF-3 and ADF-4.

Sequencing of spider silk proteins has revealed that these proteins are dominated by iterations of four simple amino acid motifs: (1) polyalanine $(Ala_n)$; (2) alternating glycine and alanine $(GlyAla)_n$; (3) GlyGlyXaa; and (4) GlyProGly $(Xaa)_n$, where Xaa represents a small subset of amino acids, including Ala, Tyr, Leu and Gln (for example, in the case of the GlyProGlyXaaXaa motif, GlyProGlyGlnGln is the major form). Hayashi, et al., J. Mol. Biol. 275:773, 1998; Hinman, et al, Trends in Biotech. 18:374 379, 2000. Spider silk proteins may also contain spacers or linker regions comprising charged groups or other motifs, which separate the iterated peptide motifs into clusters or modules.

Modules of the GlyProGly$(Xaa)_n$ motif are believed to form a β-turn spiral structure which imparts elasticity to the protein. Major ampullate and flagelliform silks both have a GlyProGlyXaaXaa motif and are the only silks which have elasticity greater than 5 10%. Major ampullate silk, which has an elasticity of about 35%, contains an average of about five β-turns in a row, while flagelliform silk, which has an elasticity of greater than 200%, has this same module repeated about 50 times. The polyalanine $(Ala_n)$ and $(GlyAla)_n$ motifs form a crystalline β-sheet structure which provides strength to the proteins. The major ampullate and minor ampullate silks are both very strong, and at least one protein in each of these silks contains a $(Ala_n)/(GlyAla)_n$ module. The GlyGlyXaa motif is associated with a helical structure having three amino acids per turn ($3_{10}$ helix), and is found in most spider silks. The GlyGlyXaa motif may provide additional elastic properties to the silk.

The biofilament proteins that are applicable to the methods according to the inventive subject matter include natural or recombinantly produced MaSpI and MaSpII proteins, as described in U.S. Pat. Nos. 5,989,894 and 5,728,810 (hereby incorporated by reference). These patents disclose partial cDNA clones of spider silk proteins MaSpI and MaSpII, and the amino acid sequences corresponding thereto. The MaSpI and MaSpII spider silk or fragment or variant thereof usually has a molecular weight of at least about 16,000 daltons, preferably 16,000 to 100,000 daltons, more preferably 50,000 to 80,000 daltons for fragments and greater than 100,000 but less than 300,000 daltons, preferably 120,000 to 300,000 daltons for the full-length protein.

The inventive subject matter may also use minor ampullate spider silk proteins, such as those disclosed in U.S. Pat. Nos. 5,756,677 and 5,733,771, and to flagelliform silks, such as those described in U.S. Pat. No. 5,994,099, and spider silk proteins described in U.S. Provisional Patent Application No. 60/315,529. These patents and applications are hereby incorporated by reference.

The sequences of the spider silk proteins may have amino acid inserts or terminal additions, so long as the protein retains the desired physical characteristics. Likewise, some of the amino acid sequences may be deleted from the protein so long as the protein retains the desired physical characteristics. Amino acid substitutions may also be made in the sequences, so long as the protein possesses or retains the desired physical characteristics.

The methods of the invention may also be used to recover natural or recombinantly produced ADF-1, ADF-2, ADF-3 and ADF-4 proteins from biological fluids. These proteins are produced naturally by the *Araneus diadematus* species of spider. The ADF-1 generally comprises 68% poly$(Ala)_5$ or $(GlyAla)_{2-7}$, and 32% GlyGlyTyrGlyGlnGlyTyr. The ADF-2 protein generally comprises 19% poly$(A)_8$, and 81% GlyGlyAlaGlyGlnGlyGlyTyr and GlyGlyGlnGlyGlyGlnGlyGlyTyrGlyGlyLeuGlySerGlnGlyAla. The ADF-3 protein generally comprises 21% AlaSerAlaAlaAlaAlaAlaAla and 79% (GlyProGlyGlnGln)n, where n=18. The ADF-4 protein comprises 27% SerSerAlaAlaAlaAlaAlaAlaAlaAla and 73% GlyProGlySerGlnGlyProSer and GlyProGlyGlyTyr.

(Abbreviations for amino acids used herein are conventional/Three-letter One-letter Amino Acid abbreviation Symbol Alanine Ala A Arginine Arg R Asparagine Asn N Aspartic Acid Asp D Asparagine or aspartic acid Asx B Cysteine Cys C Glutamine Gln Q Glutamic acid Glu E Glutamine or glutamic acid Glx Z Glycine Gly G Histidine His H Leucine Leu L Lysine Lys K Methionine Met M Phenylalanine Phe F Proline Pro P Serine Ser S Threonine Thr T Tryptophan Trp W Tyrosine Tyr Y Valine Val V.)

The inventive subject matter may be used to improve naturally occurring substrate materials, such as cotton or wool, to exhibit novel and significantly improved physical, chemical and biological properties and functionalities. Furthermore, for textile industry it is desirable to provide naturally occurring materials, such as cotton or wool, with improved strength, elasticity, bending rigidity and/or resistance to motion while retaining air permeability and wearing comfort. Under the inventive subject matter it has been surprisingly realized that silk polypeptides may be applied using certain plasma technologies to provide a highly efficient coating reaction, which enables the production of coated naturally occurring material having the desired properties mentioned above.

In the context of the inventive subject matter, a coating reaction using silk polypeptides also allows the effective attachment of molecules to naturally occurring materials to produce materials tailored for specific applications, e.g., coated textiles, clothing, and textiles for footwear having highly active surfaces providing UV-blocking, antimicrobial and self-cleaning properties. The coating may be doped to provide electrical conductivity to the coating or selected portions thereof. One example of a doping agent is iodine as well as various conductive metals. By selected doping, conductive circuits or traces may be formed in the coating for use electronics and computing or wireless applications, such as are emerging in the area of "smart clothing".

In the context of the inventive subject matter, the term "silk polypeptide" refers to a silk polypeptide or protein (it is noted that, unless otherwise indicated, these two terms, as used herein, are interchangeable) that is expressed in natural or synthetic form. It may be silk polypeptide derived from a recombinant (e.g. microbial, insect, plant or mammalian) expression system, i.e., separated from its natural milieu, (recombinant silk polypeptide or protein). Or it may be a silk polypeptide that is harvested from natural source (e.g. spider, silk worm, mussel, or fly larvae).

A "silk polypeptide" as used in the context of the inventive subject matter further refers to a polypeptide with an amino acid sequence which comprises or consists of at least 50%, 60%, 65%, 70%, 75%, 80%, 85%, 90%, preferably at least 95% and 100% of multiple copies of one identical repetitive unit (e.g. $A_2$, $Q_6$, or $C_{16}$, wherein the items 2, 6, or 16 represent the number of repetitive units) or multiple copies of two or more different repetitive units (e.g. $(AQ)_{24}$, or $(AQ)_{12}C_{16}$).

In the context of the inventive subject matter, a "repetitive unit" refers to a region which corresponds in amino acid sequence to a region that comprises or consists of at least one peptide motif (e.g. AAAAAA) or GPGQQ) that repetitively occurs within a naturally occurring silk polypeptide (e.g. MaSpI, ADF-3, ADF-4, or Flag) (i.e. identical amino acid sequence) or to an amino acid sequence substantially similar thereto (i.e., variational amino acid sequence). In this regard, "substantially similar" means a degree of amino acid identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9%, over the whole length of the respective reference naturally occurring amino acid sequence.

A "repetitive unit" having an amino acid sequence which is "identical" to the amino acid sequence of a naturally occurring silk polypeptide, for example, can be a portion of a silk polypeptide corresponding to one or more known peptide motifs of spider silk, e.g., MaSp I, MaSp II, ADF-3, and/or ADF-4. A "repetitive unit" having an amino acid sequence which is "substantially similar" to the amino acid sequence of a naturally occurring silk polypeptide, for example, can be a portion of a silk polypeptide corresponding to one or more peptide motifs of MaSpI, MaSpII, ADF-3, and/or ADF-4, but having one or more amino acid substitution at specific amino acid positions.

The "repetitive unit" does not include the non-repetitive hydrophilic amino acid domain generally thought to be present at the carboxyl terminus of naturally occurring silk polypeptides.

A "repetitive unit" according to the inventive subject matter may refer to an amino acid sequence with a length of 3 to 200 amino acids, or 5 to 150 amino acids, or a length of 10 to 100 amino acids, or 15 to 80 amino acids, or a length of 18 to 60, or 20 to 40 amino acids. For example, the repetitive unit may have a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, or 200 amino acids. The repetitive unit according to the inventive subject matter may consist of 3, 4, 5, 6, 7, 8, 9, 10, 12, 15, 18, 20, 24, 27, 28, 30, 34, 35, or 39 amino acids.

The silk polypeptide used in the methods and constructs according to the inventive subject matter may consist of between 6 to 1500 amino acids, or between 200 to 1300 amino acids, or between 250 to 1200 amino acids, or between 500 to 1000 amino acids.

Suitable silk polypeptide for use in the constructs and methods according to the inventive subject matter may consist of between 2 to 80 repetitive units, between 3 to 80 repetitive units, or between 4 to 60 repetitive units, or between 8 to 48 repetitive units, or between 10 to 40 repetitive units, or between 16 to 32 repetitive units. For example, the silk polypeptide may have 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units. The silk polypeptide may consist of 4, 8, 12, 16, 24, 32 or 48 repetitive units.

As presented above, at least two of the repetitive units in the silk polypeptide may be identical repetitive units. Thus, the silk polypeptide used in the constructs and methods according to the inventive subject matter may consist of multiple copies of one identical repetitive unit (e.g., $A_2$ or $C_{16}$, wherein the items 2 or 6 represent the number of repetitive units) or multiple copies of two or more different repetitive units (e.g. $(AQ)_{24}$ or $(QAQ)_8$). For example, 2, 3, 4, 5, 6, 7, 8, 9, 10, 11; 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 of the 80 repetitive units in the silk polypeptide used in the constructs and methods according to the inventive subject matter may be identical repetitive units.

Residues in two or more polypeptides are said to "correspond" to each other if the residues occupy an analogous position in the polypeptide structures. It is well known in the art that analogous positions in two or more polypeptides can be determined by aligning the polypeptide sequences based on amino acid sequence or structural similarities. Such alignment tools are well known to the person skilled in the art and can be, for example, obtained on the World Wide Web, e.g., ClustalW (www.ebi.ac.uk/clustalw) or Align (http://www.ebi.ac.uk/emboss/align/index.html) using standard settings, preferably for Align EMBOSS: needle, Matrix: Blosum62, Gap Open 10.0, Gap Extend 0.5.

The inventive subject matter is not limited to silk proteins, and the principles taught herein apply to other proteins. For example, wool polypeptides may be adapted for use in plasma treatments in a manner analogous to the silk polypeptide applications disclosed herein.

Figure 5:
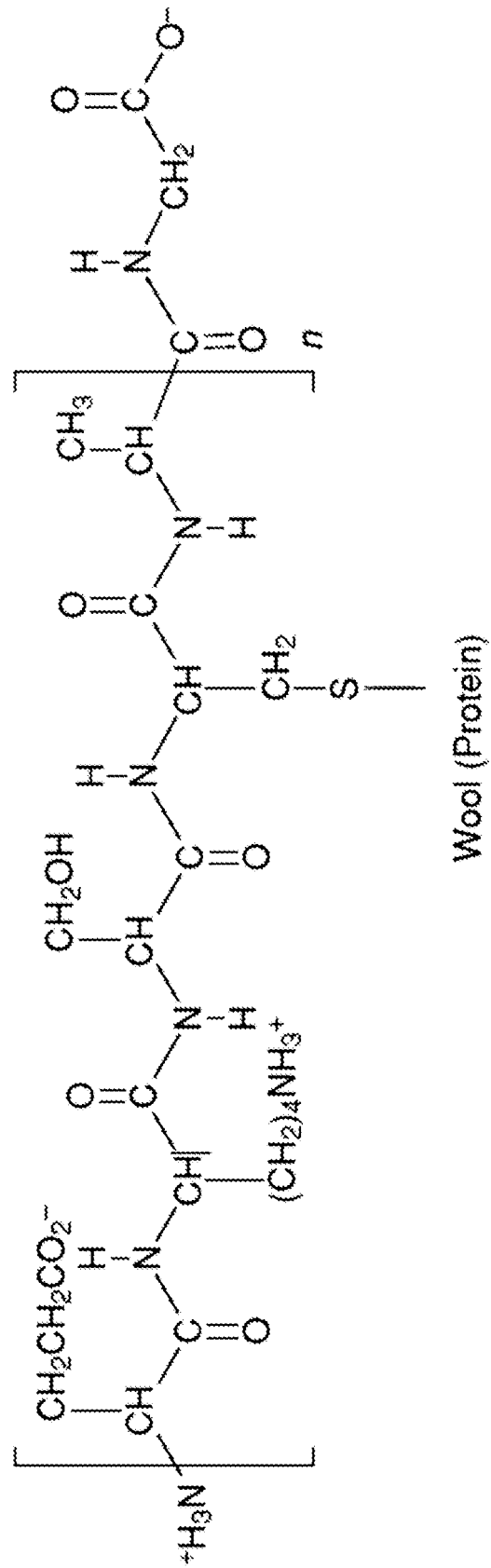
FIG. 5 shows a basic unit of wool protein.

Wool contains about 18 of the 22 naturally occurring amino acids. These acids are shown in Table 1. Chemically, wool has been estimated to have over 100 different proteins (which are combinations of amino acids in into polymer chains). A basic repeating unit of wool fabric is shown in FIG. 5. However, the structure of the wool fiber is complex, much like spider silks, so that the compositions are not uniform and have different side groups and arrangements of polymer chains. Wool's protein structure and composition varies across different animals, different breeds, and between breeds living in different geographical locations, environments, and elevations. Wool producing animals include members of the sheep and goat families. Wool itself is divided into 5 groups: fleece, pieces, bellies, crutchings, and locks. Fleece is generally used in apparel and each is processed separately. Wool has many desirable properties including, a nice hand feel and heat retention (wet or dry). It is also self-extinguishing to flames. Therefore, it may be a desirable coating for textile substrates.

Plasma Processing

Plasma is generally considered a gaseous phase of matter characterized by excited species such ions, free electrons, and an amount of visible, UV and IR radiant energy. The plasma state can be generated by electrical energy, nuclear energy, thermal energy, mechanical energy and/or radiant energy. Plasmas may be characterized by charged particle density, temperature, pressure and the presence/absence of electrical and/or magnetic fields. Plasma is generally classified as thermal or non-thermal. In thermal plasma, temperature of several thousand degrees is reached, which is destructive of textiles and other common materials. Non-thermal plasmas may be referred to as "cold" plasmas because they may be maintained at low temperatures such as between 0-100 degrees Celsius range. There are two types of cold plasma operations that can be used in textile applications: low pressure, i.e., sub-atmospheric (approximately 1-100 pa), and atmospheric (ambient) pressure.

Atmospheric plasma is available in a number of different forms: corona treatment, dielectric barrier discharge, hybrid combinations, and atmospheric glow discharge. One disadvantage of low-pressure plasma treatments is that they are performed in a contained vessel, under vacuum. Therefore, they are limited to batch processing of textiles, not continuous processing. For the speed of processing textiles in a roll-to-roll process for large volumes, batch processing is not efficient. On the other hand, with recent advances in atmospheric plasma treatments, the possibility now exists for continuous processing of textiles. Because atmospheric plasma can be a roll-to-roll process, can mimic high temperature reactions at room temperature, and requires little or no water, it is a novel, advantageous process to use for the modification of textiles.

The ionized species in plasma are generated when a voltage is placed across a gas. Radicals present in the plasma react with the surface of a substrate and/or with other species in the plasma. Plasma reactions can transform substrate surfaces in various ways. The species and energy in the plasma may be used to etch or clean a substrate surface. The plasma may enable may cause various forms of substrate surface activation. For example, the plasma conditions may cause breaking of chemical bonds; grafting of chemical moieties and functional groups, volatilizing of surface materials and removal (etching), dissociating of surface contaminants/layers (cleaning/scouring), and depositing of conformal coatings. In all these processes a highly surface specific region of the textile material (e.g., <1000 A) is given new, desirable properties without negatively affecting the bulk properties of the constituent fibers or other constituent material. To illustrate a few textile applications, surfaces may be roughened or smoothed. They may be made more hydrophobic or more hydrophilic. Chemical modification of the surface can occur by the attachment of functional groups to the substrate surface. Plasma polymerization of thin films is also an option. During the plasma process, monomers or polymers can be linked together or polymerize at the substrate surface and provide thin films of various surface and technical performance alterations. Pre-treatment and surface modification can be accomplished using only the plasma gas/substrate interaction. To apply thin films and functional groups, for instance, small amounts of the chemicals are injected via a syringe, or mist, into the plasma cloud. Certain gas plasmas are used for certain effects: argon—surface roughness modifications; oxygen—surface and surface energy modifications; ammonia and carbon dioxide—surface chemical reactivity modifications.

Figure 2:
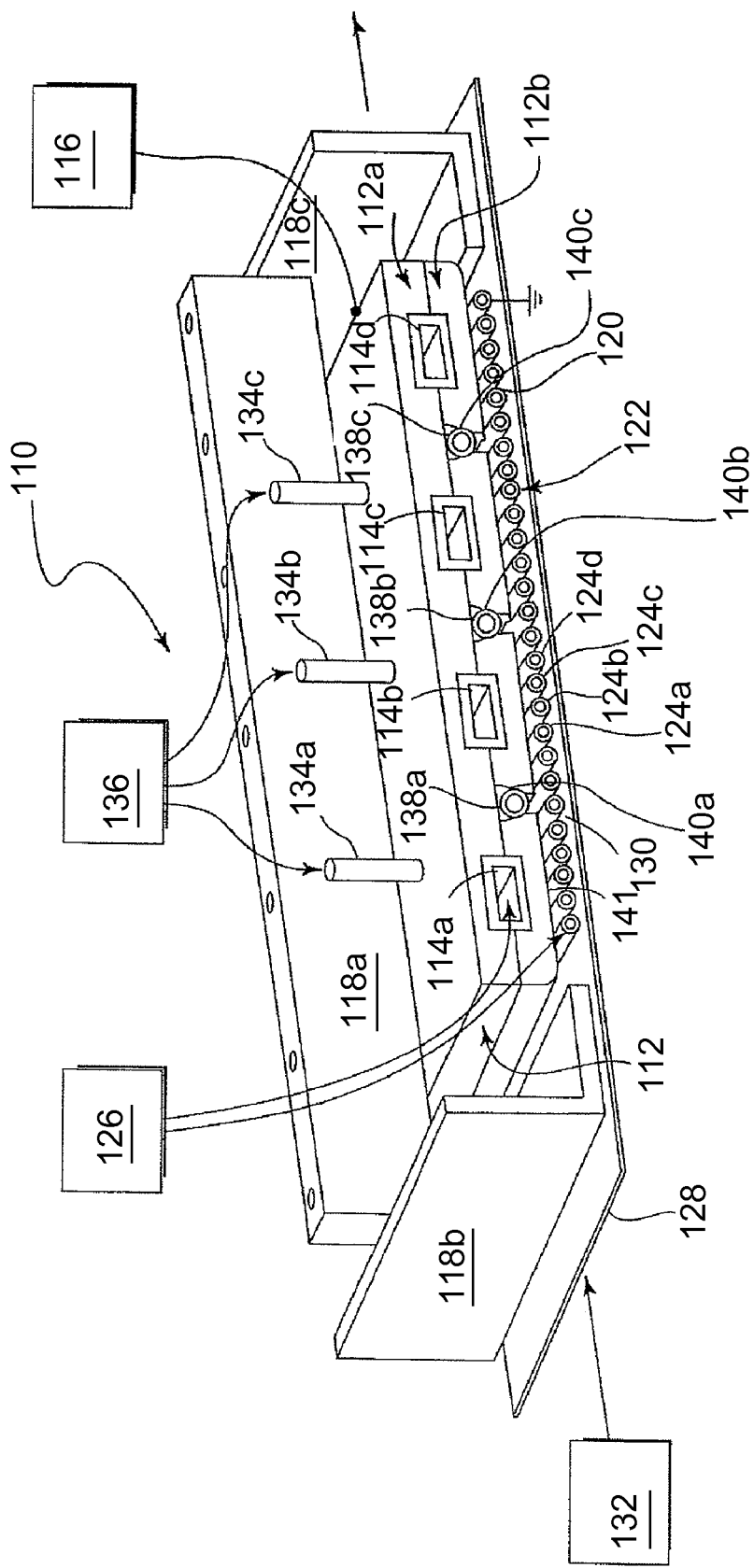
FIG. 2 is a perspective view of another possible embodiment of a prior art apparatus that may be adapted for used in a method according to the inventive subject matter of treating substrate with a biomaterial under a plasma operation.
Figure 3:
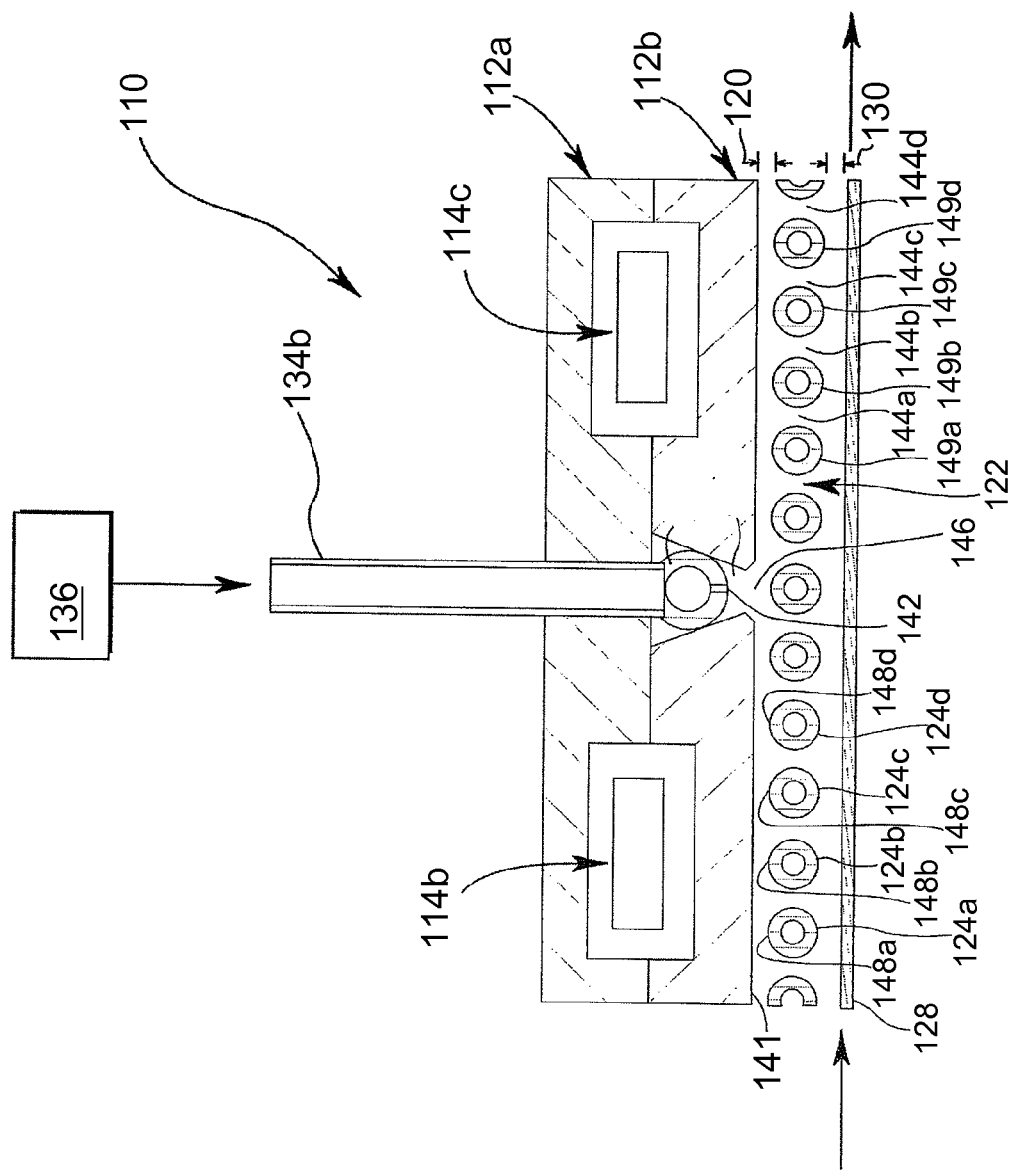
FIG. 3 is a representation of a side view of the plasma processing apparatus shown in FIG. 2.

US Patent Publication 20080107822 is directed to treatments of fibrous materials using atmospheric pressure plasma polymerization and is hereby incorporated by reference in its entirety for all purposes consistent with the teachings herein. The disclosed systems and methods may be adapted for use in providing textiles coated with polypeptides and proteins, such as the silk polypeptides contemplated herein. FIGS. 2-3, consistent with the '822 patent publication and as discussed in more detail below, show an example of a suitable system.

U.S. Pat. No. 8,361,276 discloses methods and systems for large area, atmospheric pressure plasma for downstream processing and is hereby incorporated by reference in its entirety for all purposes consistent with the teachings herein. The systems and methods in that patent may be adapted for use in coating textiles with polypeptides and proteins, such as the silk polypeptides contemplated herein. FIGS. 2-3, consistent with that patent and as discussed in more detail below, show an example of a suitable system. It may include an arcless, atmospheric-pressure plasma generating apparatus capable of producing a large-area, temperature-controlled, stable discharge at power densities between about 0.1 W/cm$^3$ and about 200 W/cm$^3$, while having an operating gas temperature of less than 50 degrees Celsius. The apparatus produces active chemical species (which may also be referred to herein as "reactive species"). The reactive species may include gaseous metastables and radicals. Such species may be used for polymerization (e.g., free radical-induced or through dehydrogenation-based polymerization), surface cleaning and modification, etching, adhesion promotion, and sterilization, as examples. The system may include, for example, either a cooled RF-driven electrode or a cooled ground electrode, or two cooled electrodes, wherein active components of the plasma may be directed out of the plasma and onto an internal or external workpiece with or without simultaneously exposing a material to the electrical influence or ionic components of the plasma.

In some embodiments, the inventive subject relates to a atmospheric pressure plasma generating apparatus for producing a large area, non-thermal, stable discharge at power densities between about 0.1 W/cm$^3$ and 200 W/cm$^3$, but also capable of having a neutral gas temperature of at most about 50° C. In what follows, the term "atmospheric pressure" means pressures between about 500 Torr and about 1000 Torr. The active chemical species or active physical species of the plasma exit the plasma discharge before impinging on a substrate disposed outside of the discharge, thereby permitting substrate surface processing, without simultaneous exposure of the substrate to the electric fields or ionic components of the plasma. As stated, the plasma has a neutral gas temperature of less than about 50° C., even during prolonged and continuous operation, and species including gas metastables and radicals, as examples, may be generated. The high power densities, the lower operating plasma temperatures and the placement of the material to be processed exterior to the plasma, permit accelerated processing rates, and treatment of most substrates. The plasma source may be used for polymerization (e.g., free radical-induced or through dehydrogenation-based polymerization), surface cleaning and modification, etching, adhesion promotion, and sterilization, as examples.

In certain embodiments, the inventive subject matter is directed to the steps of: coating the surface of the substrate textile material or other substrate with at least one polypeptide, such as a silk or wool polypeptide, that is a monomeric precursor of a polymer having the chosen characteristic, and exposing the coated substrate to the active species generated in an atmospheric pressure inert gas plasma, whereby the at least one monomeric precursor is polymerized, thereby forming the finish having the chosen characteristic. The substrate may be coated with the monomer before it is introduced into the chamber of the plasma apparatus or after.

Pulsed or unpulsed, high-power plasmas may be used to produce durable coatings that may be applied using a plasma exposure of a second or less (as opposed to minutes), and that a continuously applied, effective power density for generating thicker, more durable coatings, may be between 1 and 5 W/cm$^2$ (This is between 10$^2$ and 10$^4$ times the power density reported for prior art plasmas.) The range of effective RF frequencies may include any AC frequency that generates a "sheath" or dark space near the electrodes when capacitively coupled to the electrodes. Typical frequencies may be between 40 kHz and 100 MHz.

According to some embodiments of the inventive subject matter, a relatively thick film of a silk polypeptide monomeric precursor may be deposited onto the fabric outside of the plasma region, and the coated fabric subsequently moved into the inert gas plasma where products such as metastable and ionic species generated in the plasma induce polymerization and cross-linking of the components in the deposited film. Because the polymerization process may propagate through a relatively thick film, the process according to the inventive subject matter has a penetrating effect atypical of most plasma processes; that is, polymerization commences on the surface of the film, where it is induced by plasma-generated active species, and propagates inward into the condensed film, including regions where gas phase species produced in the plasma would not normally penetrate. In this manner, the impact of a metastable species or ionic species on the surface of the monomer may induce many polymerization events through a chain reaction in the condensed film, even at locations in the film which are not directly exposed to the plasma.

According to some embodiments of the inventive subject matter, the use of atmospheric gas plasma, such as helium plasma, as an example, avoids chemical attack or degradation of the deposited film by fragmentation. It should be mentioned that the condition of atmospheric pressure thermalizes ions produced in the plasma. Therefore, the metastable and ionic species produced in the plasma are effective for inducing polymerization and cross-linking of the components in the film, while remaining otherwise chemically unreactive. Other possible inert carrier gasses include argon, krypton, neon, and xenon may also be used as inert plasma gases.

It is well known that increasing the power applied to plasma increases the thickness of the sheath, or "dark space", around an electrode. In capacitively coupled plasma, such as that of the present claimed invention, the sheath has a time-average electric field that repels electrons. It therefore appears dark to the eye because it has a substantially reduced concentration of electrons, which generate visible emission from gas phase species by excitation through electron impact. This reduced level of electron density in the sheath inhibits dissociation of the fluorocarbon monomer. Neutral metastables that are formed in the inert gas plasma can readily cross the voltage drop of the sheath and induce polymerization.

Electrons can only transit the sheath for a short portion of the RF cycle and do so only to the extent necessary to maintain charge equalization. Positively charged ions transit the sheath and would, in a vacuum-based plasma, impact the substrate with sufficient energy (10-100 eV) to fragment the monomer, instead of simply polymerizing it. Therefore, in according to the inventive subject matter, a textile may be kept within the sheath region by placing it against either electrode or close thereto, where, high power applied to the plasma generates greater numbers of metastable species useful for initiating polymerization and cross-linking of the monomeric species condensed on the fabric, while avoiding the fragmentation of the monomer by energetic impingement of electrons or ions. In addition, plasma treatment processes for woven textiles and non-wovens may be substantially confined to the side of the substrate facing the plasma, if the substrate is held tightly against the electrode. Thus, selected treatments can be applied to one side or both sides of a fabric using a desired feedstock and carrier gas plasma to induce polymerization.

Additionally, atmospheric plasmas, as opposed to vacuum-based plasmas where a high dc bias is generated in the sheath region, effectively eliminates bombardment of the monomer on the substrate by energetic ions which would have the same destructive effect as the electron impingement. That is, in atmospheric pressure plasma, ions undergo frequent collisions with neutral gas phase species and thus do not acquire the kinetic energies they would otherwise develop in plasma operated under vacuum. In atmospheric pressure plasmas, ions are thermalized to near room temperature (about.0.03 eV, as opposed to between 10 and 100 eV for vacuum-based plasmas), rendering such species incapable of providing destructive impacts. Further, the atmospheric plasma source hereof is a "symmetric" plasma; that is, the area of the parallel RF-driven and ground electrodes are equal, and there is no grounded chamber wall contributing to the electrical behavior of the plasma. Thus, there is no DC bias, and the power density may be $>10^4$ times higher than the power density suggested in the vacuum-based plasma of U.S. Patent Application Publication No. 2004/0152381. As used herein, "atmospheric pressure" plasmas are defined as operation of the plasma at a total gas pressure sufficiently high to create a plasma sheath in which collisions are effective for thermalizing the ions crossing the sheath. Typically, this occurs at pressures between 300 Torr and 3000 Torr. It is anticipated that pressures between 600 Torr and 800 Torr will be commonly employed.

The use of an inert carrier gas plasma, such as helium, is best suited for monomers that polymerize from free radical reactions. Inert gas plasma has the advantage of being capable of triggering the free radical polymerization process without chemically modifying the resultant polymer. In some situations, however, it may be advantageous to add a minor amount of reactive gases, such as $H_2$, $N_2$, $NH_3$, or $CF_4$, as examples, to the inert gas to alter the properties, performance or composition of the resultant polymer. The use of such gases in amounts typically less than 20% of the total gas flow, may be useful to drive other forms of polymerization, such as condensation reactions or cross-linking between polymer chains. The addition of $H_2$ might be helpful in promoting the polymerization of a monomer that requires the loss of an —OH group through a condensation reaction. Similarly, the use of $N_2$ or $NH_3$ might promote crosslinking of a polymer chain, leading to greater durability for the resulting monomer.

In accordance with certain possible embodiments of the inventive subject matter, separate process modules operating at atmospheric pressure may be employed for: (1) condensing a film of biomaterial on a substrate; and (2) exposing the condensate to an atmospheric pressure plasma. Alternatively, the condensation of the biomaterial and the polymerization process may be accomplished in the same module, not separate modules. Typically this would mean keeping a constant outward flow of helium or other inert carrier gas so as to keep the monomer vapor away from the plasma region. The two-module process has benefits for providing durability of the biomaterial film on the substrate, and for avoiding unwanted film deposition on the electrodes of the plasma system. Since film deposits do not form on the electrodes, the textile treatment system may be operated continuously and with less maintenance than where the gas-phase deposition species is formed in the plasma.

Examples of textile materials include, but are not limited to, textiles made of fibers of animal or plant origin, such as wool, silk, collagen, cotton and other cellulosics, synthetic fibers such as poyolefin fibers, polyesters, polyamides (i.e., nylons), fibers from liquid crystalline polymers (e.g., aramids), polyoxymethylene, polyacrylics (i.e., polyacrylonitrile), poly(phenylene sulfide), poly(vinyl alcohol), poly (ether ether ketone) (i.e., PEEK), poly[2,2'-(m-phenylene)-5,5'-bibenzimidazole] (i.e., PBI), poly(blycolic acid), poly (glycolic acid-co-L-lactic acid, and poly(L-lactide), aromatic polyhydrazides, aromatic polyazomethines, aromatic polyimides, poly(butene-1), polycarbonate, polystyrene, and polytetrafluoroethylene, as wells as combinations of the foregoing. Such combinations may allow for enhancement of certain desired fiber properties. Typically, the textile materials or other substrates would be provided and processed as sheets or other planar forms of material. However, persons skilled in the art will appreciate that other substrates may include yarns, threads, fibers and other such filamentous materials; membranes and films, for example, those used as full, partial, or selective barrier layers that control environmental conditions, e.g., waterproofneess, water resistance, breathability, and/or windproofness. An example of a waterproof, breathable membrane material is expanded PTFE, which may be sold under the brand name GoreTex.

In addition to substrates having a planar or sheet form, or a filamentous form, the substrate could have a volumetric 3D form. For example, the form could be material on a shoe last representing some or all the volume of the shoe last. The substrate could be a backpack or other article for containing items. The substrate in planar, filamentous, or 3D form could be a foam object used in construction of footwear, apparel, backpacks and other carriers, furniture or upholstery, etc. Foamed materials include EVA and PU. The substrate could likewise be any natural or synthetic rubbers or leathers.

The composite of coated materials and substrates contemplated herein may be referred to herein as "constructs". Coatings may be affixed to the underlying substrate in a construct by any known chemical bond or bonding force, including covalent bonding, hydrogen bonding, van der Waals forces, and ionic bonding. The coatings may be applied in uniform thickness or varying thickness. In the case of the polymeric coatings, the monomeric units form a monolithic structure over the underlying portion of the substrate. In other cases, the monomeric biomaterial does not necessarily bond monomer-to-monomer but bonds monomer to substrate reactive site to form a permanent coating on the underlying portion of the substrate. (In other words, the monomers are not formally monomers but reactants combining with the substrate.) In the case of variable thickness coating, the coating thickness may be considered the average thickness on the surface. For many applications, the coating has a thickness of between 1 nm and 1 mm or 10 nm and 100 μm, or between 40 nm and 50 μm, or between 0.5 μm and 10 μm, or between 1.0 μm and 5 μm. These ranges are representative, and the inventive subject matter encompasses a wide range of thicknesses, not intended to be limited to the examples specifically given.

Coatings are typically coextensive with a desired surface area. In other words, they generally correspond to the entire surface area selected. However, this is not to say that the entire area is covered with a solid coating. The coating may be in the nature of, for example, a web, porous membrane, network of regularly spaced perforations, or other non-solid patterns that are generally coextensive with the defined surface area. The coating may have varying topology, with some areas being thicker than others. The coating may also include two-dimensional or three-dimensional features. For example, microelectronic devices, sensors, circuits or traces can be integrated into a coating to provide functional features.

For apparel applications, the coated surface area would generally be at least 6 square inches. For batch-processed rolls of materials for apparel applications, the coated surface area of the rolled material would typically be at least between about 50-72 inches in width and between about 1-100 meters in length. The roll length depends on the fabric material and construction. For example fleece would be bulky and ship in rolls of short lengths, while a 10-20 Denier downproof fabric could ship in higher length rolls. For apparel applications, such materials could be used for, in whole or part, an outer, intermediate, and/or inner layer of an apparel item.

Turning now to FIG. 1, a schematic representation of a perspective view of one embodiment of apparatus 10 for inert gas, atmospheric plasma polymerization treatment of substrates, is shown. Vessel 12, which may be heated or unheated, contains a feedstock 13, e.g., a monomeric mixture of silk polypeptide chemicals plus any desired additives. The monomeric mixture is drawn out of vessel 12 through a heated or unheated tube 16, in which valve 18 is inserted in the direction shown by arrow 20 into a heated or unheated metering pump 22. Temperatures of the various components are maintained to reagents in a liquid state. A regulated and constant flow of monomers and other chemical exits metering pump 22 through heated or unheated line 24, and is directed into an vaporizer unit 26, which converts the feedstock into a vapor, namely a gaseous, aerosol, or atomized stream of a liquid or solid feedstock. (The vaporizing unit and related steps are not necessary if the feedstock 13 held in vessel 12 is already in gas or other vapor form.) Inert gas stream 28 may be introduced into vaporizer 26 from gas source 30, to direct the flow of vapor out of vaporizer 26 and into applicator 32, which includes a slit facing fabric 34, such that gas stream 36, containing the volatilized monomers and additives is directed onto fabric, 34. Fabric or nonwoven substrate 34 is moved in the direction of arrow 38, such that the fabric is not heated by hot gas stream 36, and the volatile chemicals constantly condense onto a fresh section of fabric. The monomeric chemicals may be applied to fabric 34 inside chamber 40, which helps to keep the vapor away from plasma region 42, in order to avoid generation of unwanted chemical radicals and unwanted film deposits on electrodes 44 and 46. After condensation of the monomeric materials on the surface of fabric 34 facing the applicator 32, the fabric passes into second, atmospheric-pressure enclosure 48. Enclosures or chambers 40 and 48 include exhausts 50 and 52, respectively. The terms "enclosure and chamber" are used interchangeably. The do not necessarily mean a completely enclosed bounded space, as in a hermetic chamber. An enclosure or chamber may have open sides or openings in walls.

In enclosure 48, fabric 34 passes between electrodes 44 and 46, which are part of the atmospheric pressure plasma source, where inert gas plasma 42 is generated. This plasma, which may be continuously maintained, is operated at power levels between 0.25 and 4 W/cm$^2$. For many applications power levels between 1 and 2 W/cm$^2$ are employed. Inert gas stream 54 from source 30, which may also supply inert gas to vaporizer 26 is the plasma gas. This condensation or deposition of monomeric species followed by plasma-induced polymerization may be repeated a chosen number of times for generating multiple coats of polymer, each formed on the previous coating, for greater durability. As stated above, one or more of the plasma discharges 42 may also employ an inert gas mixture including minor additions of reactive molecules, such as $H_2$, $N_2$, $CF_4$, or $NH_3$, as examples, to promote cross-linking or other forms of polymerization reactions.

Region 56 denotes the section in which no monomer is present (polymer may be present when multiple applicators and plasmas are employed, in which case region 56 would have polymer from an earlier treatment process); region 58 identifies the section in which monomeric chemicals are applied; region 60 denotes the plasma polymerization region which cures or polymerizes or cross-links the chemicals applied by the vaporizer/applicator; and region 62 identifies the region in which the fabric has been treated at least once. Not shown in FIG. 1 are: (1) the radio-frequency plasma power supply and matching network connected to the electrodes 44 and 46, and used to power and tune plasma 42; (2) water-cooling used to cool the electrodes 44 and 46 such that the gas temperature of the plasma may be maintained at or below 70° C.; (3) the compressed gas regulators for source 30; (4) the driver and rollers used to move fabric 34 across the applicator region, into the plasma region, and out of the plasma region; and (5) the pumps in exhausts 50 and 52 for collecting and recycling the inert gas, all of which are well known to persons of ordinary skill in the art. Fabric 34 may be held against one electrode 46 to restrict the treatment process to one side thereof. Either electrode may be used for this purpose.

Although the applicator chamber or enclosure 40 and plasma chamber or enclosure 48 are shown as separate chambers or enclosures, the features and function of each may be provided under a common enclosure. For example, the applicator 32 and plasma source, i.e., electrodes 44, 46 for generating plasma region 42 could be in a single enclosure. (See, e.g., FIGS. 2-3, discussed below.) The applicator could be operated simultaneously with the operation of the plasma-generating electrodes or the applicator and electrodes could be operated sequentially. The applicator could be a separate apparatus in the system that operates independently of the feed inlet for the carrier gas. Or, it could be integrated with the feed inlet for the carrier gas such that the biomaterial and carrier gas are in a single common stream that is introduced into the common enclosure and subjected to the electrical field for generating plasma.

In addition to the single set of applicators and plasma sources, a series of applicators/plasma sources could be used to provide multiple layers of coating on a single substrate. Similarly, in a single set of an applicator/plasma source, multiple layers of coating or substrate could be applied by reversing the movement of a substrate coated after a first operation of the applicator and plasma source back to the applicator and then to the plasma source for a second operation of the applicator and plasma source.

Typical dimensions for the electrodes for an exemplary laboratory plasma apparatus are between 1 cm and 13 cm wide, by 30 cm long, with a gap of between 1 and 2.5 mm. Typical voltages may be between 120 and 450 V (peak-to-peak) at frequencies including 13.56 MHz, 27.1 MHz and 40.68 MHz.

In summary, the inventive subject matter includes the plasma-based polymerization of coatings, such as silk proteins, that are thinner or thicker than 50 nm on a surface of a textile substrate or other substrate. The inventive subject matter is suitable for a continuous operation in which the monomeric mixture is first applied to the substrate, and then the substrate that is coated with condensed monomers (neat or applied with other chemicals) is moved into an atmospheric pressure plasma, whereby an inert gas plasma is used to polymerize and cross-link the film, without destroying the monomer. By operating the plasma at sufficiently high power (>0.25 W/cm$^2$, typically between 1 and 2 W/cm$^2$), it is possible to polymerize the monomeric film at a web speed of, for example, 10-100 m/min and using a electrode dimension (in the direction of web travel) of, for example, 10-200 cm. Operation at atmospheric pressure means that pre-conditioning of the fabric to a pre-set moisture level is not necessary. It is also not necessary to pulse the plasma, thereby enabling greater throughput of the apparatus, because the duty cycle of the treatment process is 100%.

Another example of a plasma apparatus, which may be used in methods according to the inventive subject matter, is shown in FIGS. 2-3. In principle, the apparatus allows for a fast flow of active chemical or physical species generated in the plasma region between electrodes to exit the plasma region and impact workpiece (substrate) before the active species are deactivated by collisions or loss of energy, thereby generating chemical and/or physical changes to the workpiece without exposure of the workpiece to the electrical field or charged components that are present inside the plasma. This effect is achieved by creating a "plasma protrusion" from the hollow cathode effect formed between parallel openings in the ground or RF electrode and using these protrusions to assist in carrying active species further downstream from their point of generation. In the present situation, the hollow cathode effect is produced between the grounded, liquid-cooled tubular or oval electrodes that efficiently cool the electrode and through which the active species flow following generation inside the plasma. An advantage of using circular or oval tubes to form the ground electrode, as opposed to using a plurality of water-cooled rectangular or square electrodes having similar aspect ratios, is that the oval or round electrode configuration avoids sharp edges that would perturb and undesirably enhance the discharge in the vicinity of the edge, due to the locally-enhanced electrical field that would result from the relationship, $E=V/r$, where r is the radius of curvature of the edge, V is the applied, instantaneous voltage on the electrode, and E is the electric field. An enhanced electric field is likely to induce arcing. As stated above, this downstream processing approach also inhibits exposure of the workpiece to charged species formed inside the plasma because of rapid recombination of such species once they leave the plasma.

FIG. 2 is a schematic representation of a perspective view of one embodiment of plasma processing apparatus 110, is shown, illustrating RF electrode 112, having liquid cooling ducts 114a-114d, powered by RF power supply and RF matching network 116, connected to electrode 112 using a copper or other metal ribbon (not shown in FIG. 2), and supported by insulating members 118a-118c, which may be fabricated from fiberglass, G10/FR4 (McMaster-Carr), a phenolic resin PTFE, glass or ceramic, as examples, whereby first chosen spacing 120, between RF electrode 112 and planar ground electrode 122, constructed using parallel, grounded, hollow circular or oval tubes, 124a-124d, is maintained. Electrical energy is supplied in a frequency range between about 1 MHz and about 100 MHz, the RF matching network being used to adjust for a load deviation from 50 Ohms in the apparatus. Chiller 126 supplies liquid coolant to cooling ducts 114a-114d and to hollow tubes 124a-124d adapted for liquid cooling. Either rectangular or circular tubing may be used in place of cooling ducts 114a-114d. Material to be processed 128 is disposed outside of the plasma in the proximity of ground electrode 122 and maintained spaced-apart therefrom at second chosen spacing 130. Material 128 may be moved during processing using an appropriate moving apparatus 132. Gas inlet tubes 134a-134c, supplied by gas supply and manifold 136, provide the appropriate gas mixture to gas distribution tubes 138a-138c, nominally 3/8 in. O.D., there being at least one gas inlet tube 134a for each gas distribution tube 138a, as an example, to maintain approximately constant gas pressure across gas distribution tubes 138a-138c. Gas distribution tubes 138a-138c may be made from plastic, Teflon or metal, as examples. Clearly, additional inlet tubes 134 would be provided to accommodate wider RF electrodes 112. Gas distribution tubes 138a-138c have holes (not shown in FIG. 1) spaced apart along the length thereof and facing grounded electrode 122, such that gas emerges through tapered channels 140a-140c, opening out of bottom surface 141 of RF electrode 112. Tapered channels 140a-140c hold gas distribution tubes 138a-138c firmly in place, and recessed from surface 141. Radiofrequency electrode 112 is shown to be divided into two opposing portions 112a and 112b, such that the channels 114a-114d and 140a-140c may be readily machined and gas distribution tubes 138a-138c may be installed, and for cleaning and maintenance as needed during operation of discharge apparatus 110. The three gas distribution tubes 138a-138c, shown in FIG. 2, may be separated at 2.5 in. intervals center-to-center, and recessed from face 141 by 0.125 in. In another embodiment of the inventive subject matter, O-rings can be used to confine the cooling liquid to cooling ducts 114a-114c in opposing portions 112a and 112b if tubing is not employed. To prevent loss of process gas through the sides of apparatus 110, gas flow is blocked by sealing the space between the first and last of grounded tubes 124a-124d and insulating members 118b and 118c, such that the direction of gas flow is always through the opening between grounded tubes 124a-124d (not shown in FIG. 2).

FIG. 3 is a schematic representation of a side view of plasma processing apparatus 110 hereof, illustrating gas supply tube 134b, water cooling channels 114b and 114c for RF electrode 112, recessed gas distribution tube 138b, tubular ground electrode 122, and material 128 disposed downstream of the plasma which is formed in first spacing 120. Shown also are radial holes 142, which permit gas to flow out of gas distribution tube 138b, into tapered channel 140b, and out of surface 141 of RF electrode 112b. Holes 142 may be 0.03 in. in diameter. The gap between adjacent grounded electrode tubes 124a-124d may be between about 0.03 in. and 0.12 in. It is believed that between two plasma discharge apparatuses: one having an electrode gap of about 0.12 in. and another having an electrode gap of about 0.093 in., the latter apparatus, having more grounded tubes for the same size of electrode 22, will give better results for the same flow conditions. The difference may be the result of a higher "downstream" gas flow velocity achieved with the smaller gap, and better gas cooling because of the increased area of the tubes.

As stated above, effective cooling of the RF electrode may be achieved by sandwiching square copper or aluminum tubing 114a-114d between top and bottom sections 112a and 112b of RF electrode 112 which may also be made from aluminum, and flowing thermostatically-controlled, chilled water from chiller 126 which cools RF electrode 112 by conduction. Because neither RF electrode 112 nor grounded electrode 122 are covered with a dielectric material, thermal conduction between the electrodes and the gas is greatly enhanced, enabling effective and efficient gas cooling. Grounded electrode 122 includes a series of parallel, equally-spaced tubes 124a-124c through which cooling water is also flowed utilizing chiller 126. Cooling ducts or tubes 114a-114d of RF electrode 112 and tubes 124a-124d could well be cooled by other fluids, such as a glycol-based coolant, or a chilled gas, as examples. Because of the high surface area provided by tubes 124a-124d of grounded electrode 122, gas cooling is enhanced relative to a water-cooled planar electrode. For tubes having ¼ in. outside diameter (O.D.), and a gap of about 0.09 in. open area between the tubes, the increase in surface area over a planar electrode is a factor of about 2.2. Thus, the downstream gas flow onto the substrate or workpiece may be effectively cooled. When oval-shaped ground electrode tubes 124a-

124*d* are used, the short dimension of the tube is perpendicular to RF electrode 112 and the long dimension thereof is parallel to RF electrode 112.

Flowing gas is employed to generate the plasma and to carry active components produced in the plasma discharge between the RF and ground electrodes in spacing 120, out of the plasma through the spaces between the tubes 144*a*-144*d* (FIG. 2), of grounded electrode 122, and onto workpiece (substrate) 128. One gas mixture effective for this purpose includes between about 85% and about 100% helium flowing from gas supply 136 (FIGS. 2 and 3) into gas inlet tubes 134*a*-134*c* and into gas distribution tubes 138*a*-138*c*, also shown in FIGS. 2 and 3 hereof. Other gases or vaporized substances may be added to the helium flow to enhance the formation of active species inside the plasma volume. Distribution tubes 138*a*-138*c* are fitted with small openings 142 to permit the gas to exit the distribution tubes from the side of the electrode facing the plasma. By placing these distribution tubes within gap or channel 140*a*-140*c* respectively, machined into electrode 112, the distribution tubes are kept out of the active region of the plasma, as are the gas outlet openings. The channels do not permit plasma formation in immediate vicinity thereof, because the inter-electrode gap between the RF and ground electrode is too large for a discharge to occur. The gas distribution tubes are disposed away from the discharge in order to prevent arcing events that occur due to an enhanced hollow cathode effect which may occur in small openings, in a similar manner to those in micro-hollow discharges. Three rows of gas distribution tubes have been found to be sufficient to achieve uniform processing for an RF electrode 112 that is 2 m×0.3 m, the longer dimension being parallel to distribution tubes 138*a*-138*d*, as shown in FIG. 3, and with the axis of the gas distribution tubes being perpendicular to the movement of material 128.

As stated above, gas flow from the plasma is prevented from exiting the plasma region except through the narrow space between the tubes. Even though significant electrical power (between about 10 W/cm$^3$ and occasionally greater than about 100 W/cm$^3$) is deposited into the plasma, which adds thermal energy to the process gas, efficient gas cooling effected by the water cooling system and the absence of thermal insulators (such as electrical dielectric covers) on the tubes and the RF electrode keep the gas temperature low. This may be significant when the present plasma discharge apparatus is used for surface polymerization of thin-film monomers since brief exposure to a hot gas will cause condensed monomer on the workpiece to rapidly vaporize and escape from the system.

Material 128 may be moved perpendicular to the parallel alignment of the grounded electrode tubes, which provides a uniform, surface treatment because all areas of the surface are exposed to the gas flow. The gap between the material and the bottom of the tubes can also be controlled and varied. This gap is typically between about 0.5 mm and about 10 mm. A large gap enables the apparatus to polymerize monomer applied to thick substrates, such as deep-piled carpet, but also has the disadvantage that some of the active chemical species flowing out the plasma will recombine, or deactivate by other time-dependent means (such as by radiation or collisions), leading to slower processing. A small gap between the material and the tubes has the advantage of minimal deactivation of active species, but also is more prone to contaminating the plasma volume between the RF and ground electrodes by mixing of any volatile vapors from the material with the process gases. The ability to treat materials that may emit vapors from other processing steps is a significant advantage since treatment of such materials using any of the in-situ processing methods would result in contamination of the process gas by the emitted volatile vapor, or would require such high gas flow as to be prohibitive in cost. Close spacing of the tubes also allows the plasma gas to exit towards the material at a higher velocity, because the gas flow is directed through a smaller space, which increases the linear velocity of the gas, but without a concomitant increase in gas consumption, and thereby operating cost.

If the workpiece or material were to be held static in the apparatus, the result would be stripes of treatment, each stripe corresponding to a gap between the grounded electrode tubes 124*a*-124*d*. By moving the workpiece across the apparatus in a uniform manner and in a direction normal to the ground electrodes, uniform surface processing has been achieved. This provides for continuous treatment of a material, either in an in-line process or a stand-alone batch process. Workpiece or material 128 may include flexible materials such as textiles, carpet, plastics, paper, metal films, and non-wovens, as examples, or rigid materials, such as glass, silicon wafers, metal and metal sheeting, wood, composite materials, cardboard, surgical instruments or skin, as examples. The workpiece may be a laminar material.

The material may be moved using a conveyor belt, moving stage, or through other means of locomotion. Because the workpiece is outside of the plasma and the electrical fields therein, movement thereof is not complicated. The distance between the workpiece and the exit of the plasma-generated species between grounded electrode tubes 124*a*-124*d* is adjusted such that the deactivation or decay of the active species has not destroyed the chemical reactivity of the gas stream in the downstream region. Placement and movement of the workpiece between about 0 mm and about 10 mm from the surface of grounded electrode tubes 124*a*-124*d*, may satisfy this condition, depending on the process chemistry.

In summary, in one possible embodiment, stable, non-arcing operation of the plasma requires three conditions to be satisfied: (a) a flow of a process gas consisting of between about 85% and about 100% helium, for example; (b) RF excitation of one electrode in the frequency range of between about 1 MHz and about 100 MHz with bare metal electrodes exposed to the plasma; and (c) a gap between the RF-driven electrode and the ground electrode that is between approximately 0.5 mm and approximately 3 mm. It is believed that a spacing of about 1.6 mm when an RF frequency of about 13.56 MHz will obtain satisfactory results (and at slightly smaller distances for higher frequencies). Additionally, low-temperature operation (that is, between about 0° C. and about 100° C., or between 10° C.-35° C.) requires efficient cooling of both electrodes using a temperature-controlled fluid, such as chilled air, ethylene glycol or distilled water, as examples. The use of conductive fluids, such as brine, is undesirable because of the corrosive effect of the brine as well as the electrical leakage of radiofrequency power that may result.

In some embodiments, the coating of a thickness of an applied silk polypeptide on a textile substrate is between 1 nm and 1 mm, or 10 nm and 100 μm, or between 40 nm and 50 μm, or between 0.5 μm and 10 μm, or between 1.0 μm and 5 μm. These ranges are representative and the inventive subject matter encompasses a wide range of thicknesses and is not intended to be limited to the examples specifically given. 1 nm-20 nm should suffice for alterations of surface characteristics. However, thicknesses exceeding 20 nm may be needed to ensure the ability induce a tactile change in the surface of the fabric.

In some embodiments, consistent with the teachings in U.S. Pat. No. 8,016,894 for side-specific plasma treatment, one side of the coated textile may be exposed to the plasma, while the other side of the textile is maintained in close proximity to a surface impervious to the plasma species. In this manner, the plasma may selectively modify (e.g., coat) one side of the textile. The side of the fabric facing the impermeable surface is protected from modification by the chemical species generated in the plasma. It should be mentioned that whether the fabric is pressed against the impermeable surface with some force or simply adjacent to the surface, or in the vicinity thereof, will depend on how much of the protected surface can be removed or modified without rendering insignificant the difference in properties between that surface and the surface deliberately being processed or removed. To process large quantities of fabric, the textile may be moved through the plasma at chosen speeds such that the textile spends an effective amount of time in the plasma. In some situations the plasma treatment may provide functional ligands having additional desirable properties to the surface of the fabric on the side facing the plasma; the coating on the protected side is retained essentially as coated, and may have different functionality than the plasma-processed side. The present apparatus and method may therefore be used to achieve a desired dual-functionality fabric.

Feedstock

The dope or feedstock solution used in the methods according to the inventive subject matter may be a solution that includes any silk protein contemplated herein. As used herein, the term "solution" is a broad term that includes not only solutions proper but also suspensions and colloids. The solvent used for the dope solution may be any aqueous solution in which the spider silk protein is soluble or dispersible. Hereinafter, a "solvent" is any liquid that may be used for creating dissolved or dispersed particles. Similarly, references to "dissolving" and like terms, means the act of dissolving or dispersing for purposes of forming a solution proper, suspension or colloid.

The solvent may be an aqueous buffer solution with a pH from about 4 to about 12. In some cases a solution has a pH of about 11 (e.g., pH 10.6-11.3). Adjusting the pH of the dope solution to about pH 11 may reduce the formation of aggregates and result in coating layers of higher quality, that are more resistant to breakage. In one embodiment, the pH of the dope is adjusted by adding glycine.

Depending on the hydrophobicity of the silk polypeptide, the dope solution may or may not contain solubilizing agents such as hexafluoroisopropanol and other organic solvents, or guanidine hydrochloride, urea or other denaturants or chaotropic agents. Aqueous buffers that promote a liquid crystalline structure of the spider silk protein may be desired in some applications. Suitable buffer solutions for use in the dope solutions may include 50 mM glycine. Other useful buffers include, but are not limited to, PBS (phosphate buffered saline), Tris (Tris hydroxymethylaminoethane), pyrrolidine, piperidine, dialkylamines (e.g., diethylamine), homocysteine, cysteine, 6-aminohexanoic acid, CABS (N-cyclohexyl-4-aminobutane-1-sulfonic acid), 4-aminobutyric acid, proline, threonine, CAPS (N-cyclohexyl-3-aminopropane-1-sulfonic acid), β-alanine (3-aminopropanoic acid), lysine, ascorbate, trialkylamines (e.g., triethylamine), cysteic acid, and carbonate.

In other embodiments, the dope solution includes silk polypeptide dissolved in one or more non-aqueous solvents.

Normally, the dope solution is about 2-60% or more (w/v) in silk protein. The dope solution may be about 15-25% (w/v) silk protein, or about 20% (w/v). The concentration of the dope solution should be high enough to maintain the silk protein in a form suitable for coating of textiles or other work substrates, but low enough to avoid gelling and precipitation of the protein in the solution. Concentrations in excess of 15% (w/v) silk protein may be necessary to achieve the form suitable for coatings; however, at concentrations above 40%, formation of insoluble aggregates and/or disoriented spider silk fibers may occur.

The dope solution may also contain various additives to improve the stability and physical properties (e.g., viscosity) of the dope solution. These additives may be used to increase the stability of the dope or increase the crystallinity of the silk protein in solution. Such additives may allow for the coating of textiles and other substrates from dope solutions that are as high as about 45%, 50%, 60% or more (w/v) silk protein. Dope solution additives may also become incorporated into the silk protein coating on the textile other substrate to add desired properties. Typical additives of this type may include, for example, plasticizers. Another possible additive is polyethylene oxide, having a molecular weight in the range of 4,000,000-9,000,000 or greater, which can perform as a viscosity enhancer, promote stability and processability of the dope solution, and serve as an inhibitor of dope gelation. As an example of possibly suitable application, a polyethylene oxide, having a molecular weight of 4,000,000 to 6,000,000, may be added to the dope solution in concentrations of 0.03 to 2%. In another example, polyethylene oxide having a molecular weight ranging from 4,000,000 to 9,000,000, or greater than 10,000,000, if dissolvable in the aqueous solution, is added at concentrations wherein which the polyethylene oxide retains the ability to dissolve into the dope solution. The higher the molecular weights of the polymer, the lower the concentration that can be used. Typically, the ratio of silk protein to polymer in the dope solution should be no greater than 100:1.

Additives may include compounds present in the aqueous dopes that are naturally secreted by spiders such as, for example, GABamide (.gamma.-aminobutyramide), N-acetyltaurine, choline, betaine, isethionic acid, cysteic acid, lysine, serine, potassium nitrate, potassium dihydrogenphosphate, glycine, and highly saturated fatty acids. Vollrath et al., Nature 345: 526 528, 1990; Vollrath, Reviews in Molecular Biotechnology, 74:67 83, 2000. These naturally occurring additives help maintain the aqueous coating of the capture web and keep the silk proteins in favorable conformations. Thus, the web is stabilized under a variety of conditions and dehydration is prevented. Specifically, betaine and GABamide are osmoprotectives and osmolytes used by a wide range of organisms. Taurine is a protein-stabilizing compound.

Other additives which may be used in the dope solution include, but are not limited to, succinamide, morpholine, CHES (N-cyclohexylaminoethane sulfonic acid), ACES (N-(2-acetamido)-2-aminoethane sulfonic acid), 2,2,2-trifluoroethanol, saturated fatty acids such as hexanoic acid and stearic acid, glycerol, ethylene glycol, poly(ethylene glycol), lactic acid, citric acid and 2-mercaptoethylamine.

Other useful additives may be included in the coagulation bath. Additives including certain surfactants, osmoprotective agents, stabilizing agents, UV inhibitors, and antimicrobial agents are effective when added to the dope solution, or to the coagulation bath, or both. Stabilizers that protect against UV radiation, radical formation, and biodegradation include, for example, 2-hydroxybenzophenones, 2-hydroxyphenyl-2-(2H)-benzotriazoles, cifnamates, and mixtures thereof. These chemicals are capable of absorbing and dissipating UV energy, thereby inhibiting UV degradation. Free radicals are neutralized by hindered amine light stabilizers (HALS), butylated hydroxyanisole (BHA), and butylated hydroxytoluene (BHT). Antimicrobials that may be added to the spin dope include silver nitrate, iodized radicals (e.g., Triosyn; Hydro Biotech), benzylalkonium chloride, alkylpyridinium bromide (cetrimide), and alkyltrimethylammonium bromide. Viscosity enhancers may be added to improve the rheological properties of the dope. Examples include, but are not limited to polyacrylates, alginate, cellulosics, guar, starches and derivatives of these polymers, including hydrophobically modified derivatives. In a preferred embodiment, polyethylene oxide is added. In one such embodiment, polyethylene oxide, preferably having a molecular weight of 4,000,000 to 6,000,000 is added to the dope solution in concentrations of 0.03 to 2%. In another such embodiment, polyethylene oxide having a molecular weight ranging from 6,000,000 to 9,000,000, or greater than 10,000,000 is added at concentrations wherein which the polyethylene oxide retains the ability to dissolve into the dope solution. Preferably, the ratio of silk protein to polymer in the dope solution is no greater than 100:1.

The dope is normally prepared from a biological fluid derived from a transgenic organism, such as is disclosed in U.S. application Ser. No. 10/341,097, entitled Recovery of Biofilament Proteins from Biological Fluids, filed Jan. 13, 2003, which is hereby incorporated by reference in its entirety. Recombinant spider silk protein used for production of dope can be recovered, for example, from cultures of transgenic mammalian cells, plants, or animals and the dope prepared from culture media, plant extracts, or the blood, urine, or milk of transgenic mammals. Removing contaminating biomolecules (e.g., proteins, lipids, carbohydrates) from the dope, via such methods as tangential flow filtration, centrifugation and filtering, and chromatographic techniques, generally improves the properties of the spun fiber.

According to the methods of the invention, the dope solution may be produced and/or used for coating at a temperature in the range of 0° C. to 100° C. for many applications. However, the chip melting of certain materials into dope solutions may require a range of approximately 2°-380° C. The melting temperature of polypeptide materials depends on the amino acid sequences. However, to keep temperatures at the lower side of the range, a dispersion of monomers may be used instead of a chip melt.

Analogous wool polypeptide feedstocks, as well as other polypeptide feedstocks, may be created following the same general teachings as those above for silk polypeptides.

From the foregoing teachings, persons skilled in the art will appreciate that various desirable properties or characteristics may be imparted to textile materials and other substrates. Such properties or characteristics include, as used herein, include, improved: haptic or hand (e.g., fabric softening), strength, durability, elasticity, water and oil stain repellency, insect-repellency, anti-static properties, fade resistance in sunlight and lighting conditions, and antimicrobial properties to reduce odor, infection, and formation of mold or mildew.

The principles described above in connection with any particular example can be combined with the principles described in connection with any one or more of the other examples. Accordingly, this detailed description shall not be construed in a limiting sense, and following a review of this disclosure, those of ordinary skill in the art will appreciate the wide variety of lending systems and other systems that can be devised using the various concepts described herein. Moreover, those of ordinary skill in the art will appreciate that the exemplary embodiments disclosed herein can be adapted to various configurations without departing from the disclosed principles. The previous description of the disclosed embodiments is provided to enable any person skilled in the art to make or use the disclosed innovations. Various modifications to those embodiments will be readily apparent to those skilled in the art, and the generic principles defined herein may be applied to other embodiments without departing from the spirit or scope of this disclosure. Thus, the claimed inventions are not intended to be limited to the embodiments shown herein, but are to be accorded the full scope consistent with the language of the claims, wherein reference to an element in the singular, such as by use of the article "a" or "an" is not intended to mean "one and only one" unless specifically so stated, but rather "one or more". Moreover, nothing disclosed herein is intended to be dedicated to the public regardless of whether such disclosure is explicitly recited in the claims. No claim element is to be construed as "a means plus function" claim under US patent law, unless the element is expressly recited using the phrase "means for" or "step for".

Persons skilled in the art will recognize that many modifications and variations are possible in the details, materials, and arrangements of the parts and actions which have been described and illustrated in order to explain the nature of the inventive subject matter, and that such modifications and variations do not depart from the spirit and scope of the teachings and claims contained therein.

All patent and non-patent literature that may be cited herein is hereby incorporated by references in its entirety for all purposes.

The invention claimed is:

1. A construct comprising
a substrate material and a polymerized layer of a natural or synthetic biomaterial coextensively affixed to the surface of a substrate wherein the substrate comprises a textile material having a generally sheet or planar form and the biomaterial comprises silk polypeptides comprising sericin and fibroin or wool polypeptides comprising sericin and fibroin; and
wherein the polymerized layer of a natural or synthetic biomaterial is discontinuous and deposited over the substrate in varying thicknesses to impart a varying topology to the polymerized layer in the nature of a web, regularly spaced perforations or other non-solid patterns.

2. The construct of claim 1 wherein the textile material is selected from the group petroleum-based synthetic fibers textiles consisting of, but not limited to, polyester, nylon, synthetic polyurethane (in the form of synthetic leather) cellulose, and other materials used in footwear, equipment, and apparel.

3. The construct of claim 1 wherein the polymerized layer of a natural or synthetic biomaterial comprises polypeptides characteristic of a silk or wool protein type.

4. The construct of claim 3 wherein the polymerized layer of a natural or synthetic biomaterial has an average thickness of at least 1 nm-1 mm.

5. The construct of claim 4 wherein the textile material has a surface area of at least 6 square inches.

6. A construct comprising a substrate material and a polymerized layer of a silk polypeptide affixed to the surface of the substrate material wherein the substrate comprises a textile material having a generally sheet or planar form, and the polymerized layer of a silk polypeptide comprises silk polypeptides comprising sericin and fibroin or wool polypeptides comprising sericin and fibroin, wherein the polymerized layer of a natural or synthetic biomaterial is discontinuous and deposited over the substrate in varying thicknesses to impart a varying topology to the polymerized layer in the nature of a web, regularly spaced perforations or other non-solid patterns, and wherein the construct comprises a roll of materials of a roll size from 10 inches to 72 inches wide and is approximately 1-100 meters in length.

7. An item of apparel having an outer, intermediate or inner layer comprising in whole or part the construct of claim 1.

8. The construct of claim 1 wherein the substrate comprises an article having a volumetric, 3D shape.

9. The construct of claim 1 wherein the substrate comprises a natural or synthetic rubber or leather.

10. The construct of claim 1, wherein the polymerized layer includes integrated microelectronic devices, sensors, or circuits.

11. The construct of claim 1, wherein the polymerized layer includes selected doping defining an electrically conductive path.

12. The construct of claim 6, wherein the polymerized layer includes integrated microelectronic devices, sensors, or circuits.

13. The construct of claim 6, wherein the polymerized layer includes selected doping defining an electrically conductive path.

* * * * *